US012805898B2

(12) United States Patent
Rovira Soriano et al.

(10) Patent No.: US 12,805,898 B2
(45) Date of Patent: Nov. 24, 2026

(54) MEDICAL DEVICE FOR TRANSLUMINAL ACCESS

(71) Applicants: FUNDACIÓN DE LA COMUNIDAD VALENCIANA HOSPITAL GENERAL PARA LA INVESTIGACIÓN BIOMEDICA, DOCENCIA Y DE, Valencia (ES); FUNDACIÓN PARA LA INVESTIGACIÓN DEL HOSPITAL UNIVERSITARIO Y POLITECNICO LA FE DE LA COMUNIDAD VALEN, Valencia (ES); AIMPLAS ASOCIACIÓN DE INVESTIGACIÓN DE MATERIALES PLÁSTICOS Y CONEXAS, Paterna (ES)

(72) Inventors: Lucas Rovira Soriano, La Pobla de Vallbona (ES); Guido Mazzinari, Valencia (ES); Vicente Ruedas Abarca, Valencia (ES)

(73) Assignees: FUNDACIÓN DE LA COMUNIDAD VALENCIANA HOSPITAL GENERAL PARA LA INVESTIGACIÓN BIOMÉDICA, DOCENCIA Y DESARROLLO DE LAS CIENCIAS DE LA SALUD, Valencia (ES); FUNDACIÓN PARA LA INVESTIGACIÓN DEL HOSPITAL UNIVERSITARIO Y POLITÉCNICO LA FE DE LA COMUNIDAD VALENCIANA, Valencia (ES); AIMPLAS ASOCIACIÓN DE INVESTIGACIÓN DE MATERIALES PLÁSTICOS Y CONEXAS, Paterna (ES)

( * ) Notice: Subject to any disclaimer, the term of this patent is extended or adjusted under 35 U.S.C. 154(b) by 732 days.

(21) Appl. No.: 17/917,787

(22) PCT Filed: Feb. 12, 2021

(86) PCT No.: PCT/EP2021/053408

§ 371 (c)(1),
(2) Date: Oct. 7, 2022

(87) PCT Pub. No.: WO2021/204442

PCT Pub. Date: Oct. 14, 2021

(65) Prior Publication Data

US 2023/0338055 A1 Oct. 26, 2023

(30) Foreign Application Priority Data

Apr. 9, 2020 (EP) .................................... 20382289

(51) Int. Cl.
*A61B 17/3207* (2006.01)
*A61B 17/00* (2006.01)

(52) U.S. Cl.
CPC ................. *A61B 17/320725* (2013.01); *A61B 2017/00867* (2013.01)

(58) Field of Classification Search
CPC ................ A61B 17/3207; A61B 17/32; A61B 2017/320733; A61B 2017/00867;
(Continued)

(56) References Cited

U.S. PATENT DOCUMENTS 4,411,655 A * 10/1983 Schreck ............ A61M 25/0662 604/165.01
4,722,335 A * 2/1988 Vilasi .................... A61M 16/04 128/207.14

(Continued)

FOREIGN PATENT DOCUMENTS

| | | | |
|---|---|---|---|
| WO | 9503082 | A1 | 2/1995 |
| WO | 2018055450 | A2 | 3/2018 |
| WO | 2018055450 | A3 | 3/2018 |

OTHER PUBLICATIONS

International Search Report and Written Opinion issued on Apr. 26, 2021 in corresponding International Application No. PCT/EP2021/053408; 16 pages.

*Primary Examiner* — Dianne Dornbusch
(74) *Attorney, Agent, or Firm* — Maier & Maier, PLLC

(57) ABSTRACT

A medical device for enabling a communication between a target zone within a body and an outside of the body. The device includes an inner guide and an outer extending from a rear end to a distal end and having an internal cavity. The internal cavity receives the inner guide therein. The medical device shifts from a guiding position for accessing from an
(Continued)

outside of the body to the target zone to an operating position for communication between the outside of the body and the target zone. When the medical device is in the guiding position, the internal cavity of the outer tube substantially fits the inner guide for traveling together towards the target zone; and when the medical device is in the operating position, the distal end of the outer tube is at the target zone and the rear end of the outer tube is outside the body.

17 Claims, 10 Drawing Sheets

(58) Field of Classification Search
CPC ............ A61B 1/00147; A61B 1/00148; A61B 1/00149; A61M 25/00; A61M 25/02; A61M 25/04; A61M 25/09; A61M 2025/09125; A61M 2025/09141; A61M 2025/0915; A61M 2025/09158
See application file for complete search history.

(56) References Cited

U.S. PATENT DOCUMENTS 6,090,072 A * 7/2000 Kratoska ............ A61B 17/3439 604/164.01
6,706,017 B1 * 3/2004 Dulguerov .......... A61M 16/085 128/207.29
8,337,518 B2 * 12/2012 Nance ................ A61B 17/3478 606/194
10,272,231 B2 * 4/2019 Kick ................. A61M 25/0662
10,279,124 B2 * 5/2019 Eckert ................... A61M 5/329
2005/0038408 A1 * 2/2005 von Segesser ...... A61M 1/3661 604/523
2005/0131343 A1 6/2005 Abrams et al.
2005/0209627 A1 * 9/2005 Kick ..................... A61M 29/02 606/191
2006/0200188 A1 * 9/2006 Nance ............... A61M 25/0662 606/198
2011/0282156 A1 * 11/2011 Lenker ............... A61B 17/3439 600/208
2017/0020542 A1 * 1/2017 Martin ...................... A61F 2/88
2020/0030559 A1 * 1/2020 Avniel .............. A61M 16/0434

* cited by examiner

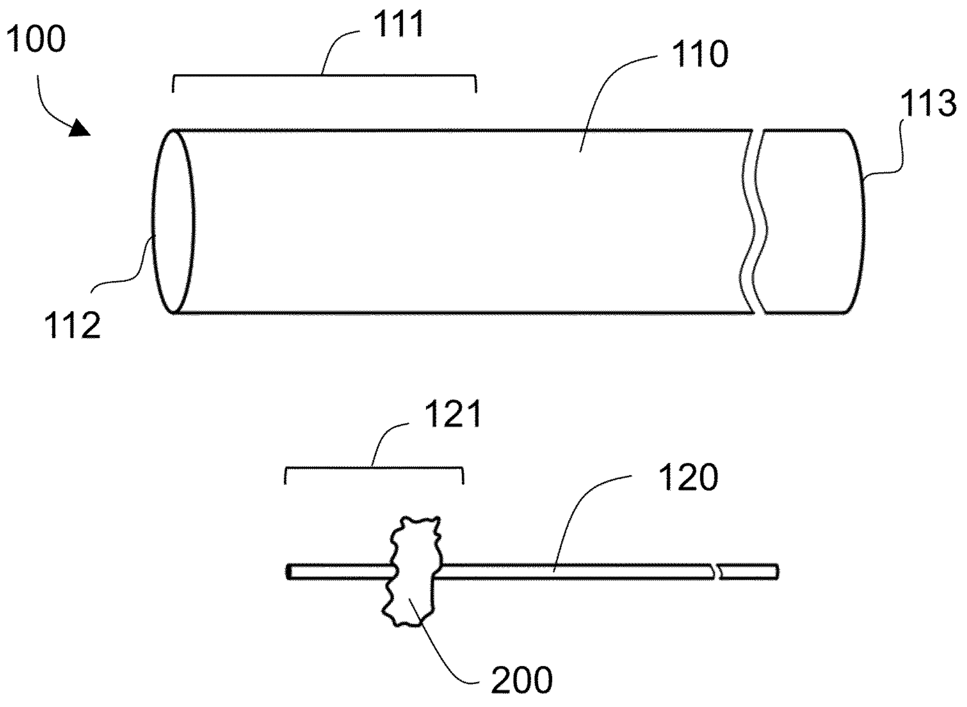
FIG. 6
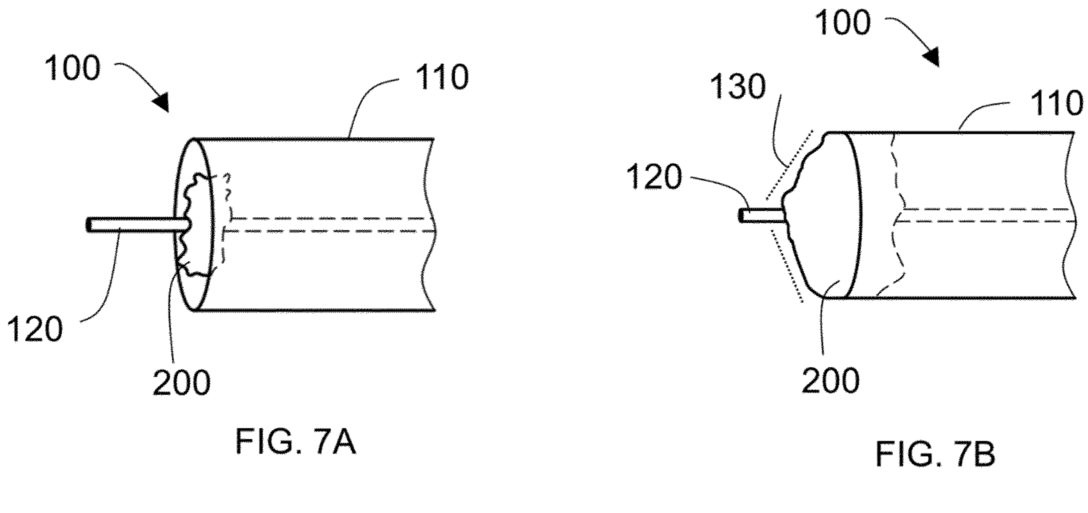
FIG. 7A
FIG. 7B

MEDICAL DEVICE FOR TRANSLUMINAL ACCESS

This application claims the benefit of the European Patent Application EP20382289.5 filed on Apr. 9, 2020.

The present disclosure is related to medical devices, more specifically to medical devices for providing transluminal access to the body.

BACKGROUND

Some medical procedures may require accessing a corporal conduit to communicate the exterior with a corporal conduit or cavity, such as canalizing a bladder through a urethral catheterization or the intubation of a patient through a tracheal catheterization. Some corporal conduits such as the bladder, the trachea, a vein, the oesophagus, etc may thus be necessary to be accessed. Currently, techniques involve using several devices and performing several steps requiring more than one practitioner operating simultaneously, which renders the access manoeuvre complex or complicated and time-consuming.

In addition, the access to a corporal conduit may be difficult to achieve in some cases, e.g. during tracheal intubation, the glottis, i.e. the anatomical space between the vocal cords, may be narrow and difficult to be accessed. The manoeuvre(s) may thus be repeated several times to be successful, which increases the probability of injuring the patient.

One way to facilitate the catheterization of a corporal conduit may be using a relatively small diameter catheter to allow passing through narrow corporal conduits. However, smaller diameter catheter may not be adequate for creating a suitable accessing to a corporal conduit. To create an effective communication between a corporal conduit and an exterior of a human body larger diameter may be generally desired.

In some examples, a guide with a reduced diameter may be inserted through the corporal conduit and then an outer tube with a larger diameter slide around the guide to reach the desired position. This manoeuvre is known as the Seldinger technique.

Furthermore, even after successfully accessing a conduit, the medical device can be displaced, i.e. may be difficult to maintain in place, and further manoeuvres to regain access may therefore be required thereby increasing the risk of injuring the patient and also the lapse of time needed to place the device correctly.

In conclusion, it would be desirable to provide a medical device to transluminal access a corporal conduit which can be operated by a single practitioner, which is easy and quick to use while at the same time less likely to injure the patient, decreasing the number of potentially dangerous steps during the manoeuvre and being reliable and cost-effective to manufacture.

SUMMARY

In a first aspect, a medical device for enabling a communication between a target zone within a body and an outside of the body is provided. The medical device comprises an inner guide and an outer tube extending from a rear end to a distal end and having an internal cavity, wherein the internal cavity is configured to receive the inner guide therein. The medical device is configured to shift from a guiding position for accessing from an outside of the body to the target zone to an operating position for enabling the communication between from the outside of the body and the target zone; wherein when the medical device is in the guiding position, the internal cavity of the outer tube substantially fits the inner guide for traveling together towards the target zone; and wherein when the medical device is in the operating position, the distal end of the outer tube is at the target zone and the rear end of the outer tube is outside the body. Furthermore, the inner internal cavity of the outer tube is configured to change in shape in response to a trigger to release the inner guide from the outer tube, thereby shifting the medical device from the guiding position to the operating position.

As the internal cavity of the outer tube substantially fits the inner guide when the medical device is in the guiding position, the inner guide and the outer tube may be simultaneously inserted into the body to reach a target zone. A compact medical device may thus be obtained when the medical device is navigating inside the body, e.g. a human body, towards a target zone.

A target zone within a body or a zone to be treated may be a corporal conduit or a corporal cavity. For example, a target zone may be at the trachea, at the bladder, at a vein or artery or at the oesophagus or cerebral or cardiac cavities, among other corporal conduits or corporal cavities.

The outer tube and the inner guide may travel together towards the target zone through an anatomical corporal conduit and/or through body tissues creating an artificial corporal conduit. For example, if the target zone is at the trachea, the outer tube and the inner guide may be inserted through the mouth and reach the trachea passing through the larynx. For instance, the target zone may be a specific vein. In that case, the outer tube and the inner guide may be inserted into the body through an incision and then may travel towards the vein through different body tissues, e.g. skin.

To reach the target zone, the outer tube and the inner guide may pass through a narrow region of the body, e.g. through the vocal cords. When the outer tube has reached a target zone, a trigger causes a change in the shape of the internal cavity of outer tube. The cross-section of the internal cavity may thus increase to remove the inner guide and then to create a fluid communication between the target zone and an outside of the body, e.g. a transluminal access, with a suitable cross-sectional dimension.

The outer tube with a reduced cross-section thus enters into the body, e.g. through a corporal conduit, and then, when the outer tube reaches a position to create a fluid communication between the target zone and the outside of the body, the internal cavity of the outer tube increases its cross-section in response of a trigger. This increase of the cross-section of the internal cavity of the outer tube allows the inner guide to be released from the outer tube and then to be removed from the body. After removing the inner guide, the outer tube may thus establish a fluid communication between the target zone and an outside of the human body. The cross-section of the internal cavity of the outer tube is greater after the change of shape caused by the trigger so as to improve the fluid communication between the target zone and the outside of the body. The outer tube may thus be a transluminal catheter communicating the target zone and the outside of the body. A fluid communication between a target zone and an outside of the body, e.g. transluminal access, may thus be created even in narrow and tortuous corporal conduits in a simple way. In addition, the risk of injuring the patient may be significantly reduced. Furthermore, in case of cutting body tissues to create a passageway, i.e.an artificial conduit, towards the target zone, the cross-section of this passageway may be reduced. As the cross-section of the incision may be reduced, risk of injuring the patient may consequently be reduced.

In some examples, the inner guide is removable from the outer tube when the shape of the internal cavity of the outer tube changes in response to the trigger. The change of the shape of the internal cavity, e.g. an increase of the diameter, allows releasing the outer tube from the inner guide for shifting the medical device from the guiding position to the operating position so as to create a transluminal access communicating the target zone and the outside the body of the patient. A communication between outside the body and a region inside the body may thus be established through the outer tube.

Contrary to other medical devices as stents, when the medical device according to this disclosure is in the operating position, the rear end of the outer tube is outside the body of the patient so as to create a fluid communication between an outside and an inside of the patient's body. For example, the stents are completely inserted inside the patient's body and are fenestrated) so that are not able to create a fluid communication between its ends.

The outer tube may engage the inner guide when the medical device is in the guiding position, i.e. when the inner guide and the outer tube travel to the target zone. The internal cavity of the outer tube may fit or match an outer surface of the inner guide. The outer tube may thus be connected to the inner guide when the medical device is in the guiding position. In some examples, the outer tube may surround or coat the inner guide when the medical device is in the guiding position. An inner surface of the internal cavity of the outer tube may contact the outer surface of the inner guide around its whole perimeter.

In some examples, a region of the inner surface defining the internal cavity of the outer tube may contact a region of the outer surface of the inner guide. In these examples, the shape of internal cavity may be slightly different to the outer surface of the inner guide. These regions in contact may be sufficient for connecting the outer tube to the inner guide. As in other examples, the trigger causes a change of the internal cavity of the outer tube so as to disengage the outer tube from the inner guide to remove the inner guide from the body of the patient.

In some examples, the change in shape of the internal cavity of the outer tube comprises increasing an inner diameter of the internal cavity. In some examples, the inner diameter may increase along a length of the outer tube. In some examples, the inner diameter may increase from the rear to the distal end of the outer tube. In some examples, the inner diameter may uniformly increase.

In some examples, the shape of the internal cavity may non-uniformly change upon receiving the trigger. For example, the cavity may comprise a first region deforming in a different degree than a second region.

In some examples, the change in shape of the internal cavity of the outer tube comprises changing the shape of an outer surface of the outer tube. Accordingly, the internal shape and the outer shape of outer shape may change. In some of these examples, the change of the shape of the outer surface may comprise increasing an outer diameter of the outer tube. A thickness defined between the internal cavity and the outer diameter of the outer tube may thus be maintained substantially constant. In other examples, the thickness defined between the inner diameter and the outer diameter of the outer tube may be reduced.

In some examples, even when the outer diameter of the outer tube increases upon the trigger, the outer diameter may be smaller than a corporal conduit used to at least partially reach the target zone. The outer tube does not exert a pressure against the corporal conduit. Contrary to other types of medical devices, e.g. stents, that expands the corporal conduit, a gap may be created between the corporal conduit and the outer tube.

In some examples, the outer tube may comprise a securing element, e.g. an inflatable cuff, arranged at the outer surface of the outer tube which may, upon deployment, block the conduit and/or securely fix the outer tube to the target zone, e.g. in to a corporal conduit as the trachea.

In some examples, the trigger to cause a change of the shape of the internal cavity of the outer guide comprises at least one of a temperature variation, a voltage variation, a pH variation and a pressure variation. In some examples, a combination of triggers may be used for causing a change of the shape of the internal cavity of the outer tube.

In some examples, the trigger may be transmitted by the inner guide. In some examples, the trigger may be generated by reaching the target zone having a specific temperature or pH. In these examples, the medical device may be controlled with a single hand which reduces the number of required practitioners to hold and manipulate the medical device. Both time and costs may therefore be reduced.

In some examples, the inner guide may cause a temperature variation in the outer tube. For example, the inner guide may transmit an increase of temperature. The shape of the internal cavity of the outer tube may be changed in response to this increase of temperature. In some examples, a temperature variation may be a variation greater than 5° C. In some examples, a temperature variation may comprise exceeding a predetermined temperature, e.g. exceeding 36° C. In some examples, the corporal temperature at the target zone may trigger the change of the shape of the internal cavity of the outer tube. In other examples, the corporal temperature at the target zone may also collaborate with the inner guide in triggering the change of the shape of the internal cavity.

In some examples, the inner guide comprises a heater to generate a temperature variation on the outer guide when the medical device is in the guiding position. The heater may be arranged in a wall defined between an outer surface and an inner surface defining an internal passageway of the inner guide.

In some examples, the heater comprises an electrical resistance, e.g. an electrical wire, embedded in the wall of the inner guide. The electrical resistance may be arranged adjacent to the outer surface of the inner guide. In some examples, the heater may comprise a plurality of electrical resistances. The electrical resistance may be heated by Joule effect. The electrical resistance may be connected to an electrical source. The electrical source may be integrated within the medical device or may be apart from the medical device. The heat generated within the inner guide may thus be transferred to the outer tube to cause a change of the shape of its internal cavity.

In some examples, the heater comprises a thermal fluid path for flowing a fluid flow at a predetermined temperature therethrough. A fluid having a predetermined temperature may thus circulate along the thermal fluid path. In some examples, the fluid may heat the outer tube. In some examples, the fluid may cool the outer tube. In these examples, the fluid flowing through the thermal fluid path may generate a temperature variation on the outer tube. In some examples, the heater may comprise a plurality of thermal fluid paths. The thermal fluid path(s) may be embedded in the wall of the inner guide. In some examples, the fluid may be air. A fluid pump may force a fluid having a predetermined temperature to flow through the thermal fluid path(s). A heat generator or a cool generator may adjust the temperature of the fluid to be pumped towards the thermal fluid path. In some examples, the medical device may comprise the fluid pump and/or the heat or cool generator.

In some examples, the inner guide comprises a pair of electrically conductive elements in contact with an inner surface defining the internal cavity of the outer tube when the medical device is in the guiding position to generate a voltage variation through the outer guide. These electrically conductive elements may be connected to an electrical source. A voltage difference may be created between these two electrically conductive elements. An electric current path may thus be generated therebetween. This electric current may pass through the outer guide. In some examples, the inner guide may comprise a plurality of pairs of electrically conductive elements. In this way, a plurality of electric current path may be generated in the outer tube. Deformation of the outer tube may thus be more homogenous.

In some examples, a pressure exerting element is arranged around the inner guide to exert a pressure on the outer guide. The pressure exerting element may be a deformable layer arranged around the outer surface of the wall of the inner guide. The pressure exerting element may outwardly deform around the wall of the inner guide. This deformation may act against the internal cavity of the outer tube. A pressure fluid may flow through the inner guide to expand the pressure exerting element.

In some examples, the pressure exerting element may be heated, e.g. electric current or a heated fluid flowing. The pressure exerted by the pressure exerting element may be combined with heat to trigger the change of the shape of the outer tube.

In some examples, a pH variation may comprise exceeding a predetermined pH value. The change of the shape of the outer tube may be trigger by reaching a part of the body exceeding this predetermined pH value.

In some examples, the outer guide comprises a shape-memory material. A shape-memory material is a material having the ability to return from a deformed shape (temporary shape) to an original shape (permanent) induced by a trigger or an external stimulus. Examples of shape-memory materials may be PLC-PLLA, polyurethane, or similar. Before inserting the outer tube together with the inner guide into the patient's body, the outer tube may be deformed to substantially fit the inner guide. The shape of the outer tube engaging the inner guide may thus be temporary. This temporary shape may be maintained by keeping the outer tube under certain conditions, e.g. keeping the outer tube at predetermined temperature range.

Appling the trigger on the outer guide comprising a shape-memory material may induce the outer guide to return to its original shape (before inserting the inner guide inside the outer tube). For example, the trigger for returning the outer guide to its original shape may be turning off the heater so as to create a temperature variation. In other example, the trigger may be stopping the generation of electrical current paths through the outer tube.

In some examples, before engaging the outer tube with the inner guide, the outer guide comprises an internal cavity with an initial cross-section. To engage the outer tube with the inner guide, the outer guide may be arranged around the inner guide and then may be stretched so as to shrink the internal cavity of the outer tube. This reduction of the internal cavity allows the internal cavity of the outer tube to fit the outer surface of the inner guide. Then, the outer tube and the inner guide may be inserted into the body of the patient and a trigger may be applied to the outer tube to change the shape of the interval cavity of the outer tube. The shape of the internal cavity of the outer tube after experiencing the trigger substantially corresponds to the initial cross-section, i.e. before coupling the outer guide to the inner guide. The shape of the outer tube may thus return to its initial shape after the application of the trigger. As the cross-section of the internal cavity after the application of the trigger is greater than the outer cross-section of the inner guide, the inner guide is decoupled from the outer tube. The inner guide may thus be completely removed from the outer tube. As a result, the internal cavity of the outer tube may thus create a passageway between the outside of the body and the target zone. The outer tube may then be used as e.g. a transluminal catheter.

In other examples, the outer tube may be connected to the inner guide by folding the outer tube around the inner guide. The outer tube folded around the inner guide may comprise ridges and valleys. The valleys contact the outer surface of the inner guide. In this way, a frictional force between the valleys and the outer surface of the inner guide promotes the connection between the outer tube in folded state and the inner guide. The ridges and the valley may extend along the longitudinal axis of the outer tube. The application of the trigger causes the outer tube to deploy and to substantially return to its initial shape. The trigger thus causes a change of the internal cavity of the outer tube so as to disengage the outer tube from the inner guide. After disengaging the outer tube from the inner guide, the inner guide may thus be removed from the body of the patient.

The shape-memory material may be a polymeric material. This polymeric material may comprise a polymer selected from the group consisting of natural polymers: collagen, gelatin, polysaccharides, poly(3-hydroxyalkanoate)s and poly(3-hydroxyvalerate)s, cellulose, collagen, as well as synthetic polymers: chemical derivates of collagen, polyphosphazenes, poly(vinylalcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidones, polyesters, polyester amides, polyanhydrides, polyaryletherketones, polycarbonates, polylactides, polyglycolides, polynorbornene polysiloxanes, polycyclooctene, polyorthoesters, polyurethanes, epoxy, thiol based, fluorinated polymers, ethylene-vinyl acetate (EVA) and their derivates and mixtures thereof.

In further examples, the shape-memory material may be a polymer comprising thermoplastic poly(ester urethane)s copolymers (PUs) and their derivates.

In other examples, the shape-memory material may be a polymer comprising polyesters such as Poly-L-lactic acid (PLLA); Poly-L-lactic acid-polyglycolic acid (PLLA-PLGA) copolymer, Poly(D,L-lactide-co-trimethylene carbonate) copolymers; polycaprolactone-poly lactic acid copolymers; oligo(ε-caprolactone)diol (OCL); oligo(p-dioxanone)diol (ODX); polyesther-polyol and their derivates and mixtures thereof.

In other examples, the shape-memory material may be a polymer comprising UV curable glassy thermoset such as poly(ethylene glycol)mono-methylether-monomethacrylate (PEGMA), poly(caprolactone)dimethacrylate; poly(D,L-lactide-co-trimethylene carbonate) dimethacrylate and their derivates and mixtures thereof.

In some examples, the inner guide may be a tube comprising an internal passageway for inputting and outputting fluids from the corporal conduit thereby allowing a fluid flow also when the medical device is being guided to the target zone.

In some examples, the medical device may further comprise a control casing having a plurality of actuators and a gripping area for being held with a single hand thereby allowing holding the casing and actuating the plurality of actuators with a single hand. The medical device may, therefore, be more easily handled by a single practitioner with a single hand which saves time while also facilitates the insertion, guide and use of the medical device. The plurality of actuators may comprise a trigger actuator, a bendable portion actuator and/or a fluid flow actuator.

In a second aspect, a medical device for enabling transluminal access to a corporal conduit, i.e. for enabling a communication between a target zone within a patient's body and an outside of the patient's body, is provided. The device comprises an inner guide comprising a distal end portion, an outer tube configured to receive the distal end portion of inner guide therein; and a pressure-exerting element arranged at the distal end portion of the inner guide. The outer tube comprises a distal end portion. The pressure-exerting element is configured to exert pressure to the distal end portion of the outer tube for releasably coupling the inner guide with the outer tube.

By using a pressure-exerting element for releasably coupling the inner guide and the outer tube together, a simultaneous insertion of both elements into a corporal conduit, may be achieved. Also, such simultaneous insertion may enable a joint guiding of both elements through the corporal conduit, in contrast to current procedures which require sequential steps. The medical device according to the present disclosure may reduce both the complexity and the time needed to place the device successfully in the target zone.

Furthermore, as the entire device may pass through a narrow stretch of the corporal conduit, the risk of injuring the patient may be significantly reduced. In some examples, the outer diameter of the outer tube may be compact or shrunk while the medical device is passing through the narrow stretch and, may be afterwards expanded due to the pressure-exerting element located at the inner guide or by a trigger.

In other examples, the diameter of the outer tube may be greater than the diameter of the inner guide, so there may be a gap between both tubes. The pressure-exerting element may expand thereby forming a gradually increasing diameter gradient between the outer tube and inner guide. Thus, facilitating the simultaneous insertion of both elements.

Besides, the use of such pressure-exerting element also enables controlling the medical device with a single hand which reduces the number of required practitioners to hold and manipulate the device. Both time and costs may therefore be reduced.

In an example, the pressure-exerting element may be configured to switch between a deployed state for coupling the inner guide with the outer tube, and an undeployed state for decoupling the inner guide from the outer tube. Depending on the state of the pressure-exerting element the engagement between the inner guide and outer tube may vary and thus, a releasable coupling may be quickly and reliably implemented.

In an example, the inner guide may be a tube comprising an internal passageway for inputting and outputting fluids from the corporal conduit thereby allowing a fluid flow also when the medical device is being guided to the zone to be treated, i.e. the target zone.

In an example, the medical device may further comprise a control casing having a plurality of actuators and a gripping area for being held with a single hand thereby allowing holding the casing and actuating the plurality of actuators with a single hand. The medical device may, therefore, be more easily handled by a single practitioner with a single hand which saves time while also facilitates the insertion, guide and use of the medical device.

In an example, the pressure-exerting element of the inner guide may be configured to trigger the outer tube expansion, thus shifting the medical device from the guiding position to the operating position. In some examples, other portions of the outer tube may also be expandable, e.g. the whole outer tube may be expandable. In some examples, the pressure-exerting element may cause and/or further accelerate the expansion of the distal end portion and, additionally, of the remaining portion of the outer tube.

By using an outer tube comprising a distal end portion to be expanded upon a pressure or upon a trigger, the outer diameter of the distal end portion of the outer tube may, before being expanded, be compact, i.e. slightly greater than the outer diameter of the inner guide. The overall outer diameter of the distal end portion of the inserted device may, therefore, be reduced thereby obtaining a compact medical device which further reduces the risk of injuring the patient and also facilitates the navigation of the device and the simultaneous insertion of the inner guide and the outer tube.

In addition, upon expansion of the outer tube, the corporal conduit may be blocked or obstructed which may prevent the entry of undesirable fluids into the conduit, e.g. to prevent stomach-fluids from entering into the trachea. Alternatively, or additionally, the outer tube may comprise a securing element, e.g. an inflatable cuff, arranged at the outer wall of the outer tube which may, upon deployment, block the conduit and/or securely fix the outer tube in the conduit.

In some examples, the expansion of the expandable portion of the outer tube may be triggered by heat. In such examples, the heat may be induced either by an electric current or by a heated fluid, which flow through the inner guide. In some examples, the outer tube may be made of a material that expands upon a trigger e.g. a shape-memory material.

A safer and more reliable medical device may thus be obtained. Furthermore, by using an outer tube having a distal end portion which is expandable, the medical device is more secure and compact, which reduces the risk of injuring the patient as the expansion may occur once the medical device is in place, instead of having an expanded outer tube when inserting and guiding the device.

In an example, the pressure-exerting element may be configured to exert a pressure to the distal end portion of the outer tube to set the medical device into the guiding position, i.e. to releasably couple the inner guide and the outer tube together. That is, in the guiding position the inner guide and the outer tube may be in contact which allows inserting the inner guide and outer tube together. Also, by being in contact, the transmission of a trigger to the outer tube (either from the inner guide or from the pressure-exerting element itself) is enabled.

In some examples, the pressure-exerting element may be configured to transmit a trigger, e.g. heat from a heated fluid or electrical current, from the inner guide to the outer tube. The trigger may enable turning the outer tube into an expanded state.

The outer tube may be made of a shape-memory material e.g. PLC-PLLA, polyurethane, or similar; that may, upon receiving a trigger, return to an original shape which may be greater than the shape upon insertion i.e. it may be expanded. The trigger may be heat from a heated fluid, a magnetic field, an electric current or any other suitable trigger.

The outer tube may comprise any of the examples of shape-memory materials described in connection with the first aspect of the present disclosure.

The inner guide and/or the pressure-exerting element may comprise a heat or electrically conductive wire or any other suitable element that enables triggering the expansion. Alternatively, or additionally, the inner guide and/or the pressure-exerting element may comprise a lumen that enables the flow of a heated fluid.

In an example, the diameter of the outer tube before being expanded may be 1-2 mm greater that the diameter of the internal guide, upon expansion, e.g. by receiving a trigger, the outer tube may recover a predefined diameter that may be greater that the diameter at the guiding position. In such examples, prior to the expansion, the pressure-exerting element may contact both the inner guide and the outer tube thereby facilitating the transmission of heat or an electrical current from the inner guide to the outer tube.

In an example, the pressure-exerting element may be in a deployed state for coupling the inner guide with the outer tube when the medical device is in the guiding position. In the deployed state the pressure-exerting element may comprise a projecting portion projecting from the distal end portion of the outer tube towards the distal end portion of the inner tube, thereby forming a gradually increasing diameter gradient.

By having a gradually increasing diameter gradient, the outer tube (and thus the whole medical device) may be more easily introduced and guided through a corporal conduit which reduces the risk of injuring the patient internally. Furthermore, the outer tube may be more precisely placed in the zone to be treated or target zone. Besides, the manufacturing costs of the medical device may be reduced as a conventional or commercially available outer tube, e.g. a standard endotracheal tube, may be used together with the inner guide.

The outer tube according the first and/or the second aspect of this present disclosure may be configured to function as an endotracheal tube, a urinary catheter, pleural effusion drainage catheter, cerebrospinal liquid drainage catheter or an intravascular line.

BRIEF DESCRIPTION OF THE DRAWINGS

Particular embodiments of the present device will be described in the following by way of non-limiting examples, with reference to the appended drawings, in which:

FIG. 6 schematically illustrates an exploited view of a medical device according to an example of the second aspect of the present disclosure.

FIG. 7A schematically illustrates the distal end portion of a medical device according to an example of the second aspect of the present disclosure having a pressure-exerting element undeployed.

FIG. 7B schematically illustrates the distal end portion of a medical device according to an example of the second aspect of the present disclosure having a pressure-exerting element deployed.

DETAILED DESCRIPTION

Figure 1A:
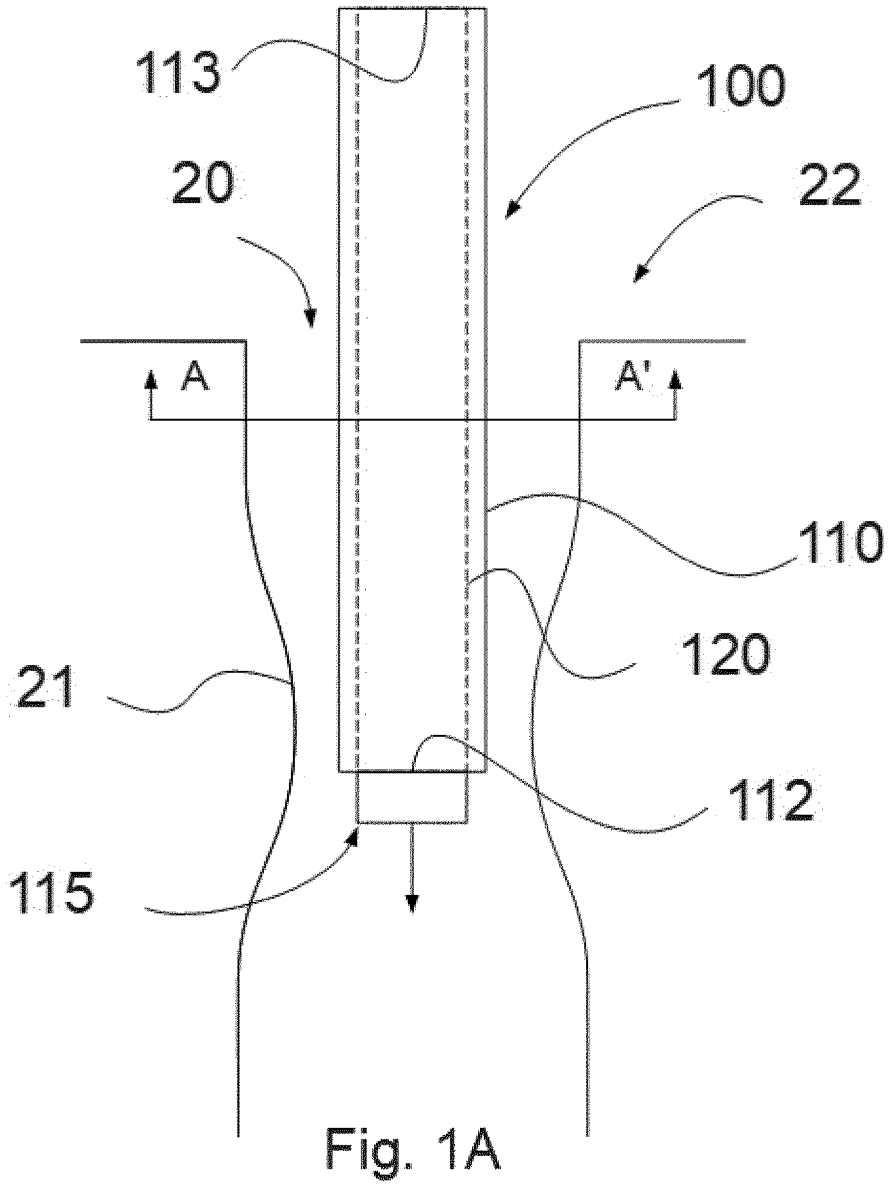
FIG. 1A schematically illustrates a medical device in the guiding position according to an example of the first aspect of the present disclosure.

To clarify some of the terms used throughout the present description and claims some definitions will be given.

The term "transluminal device" is to be understood as a device that, once successfully placed in the zone to be treated, comprises part of it inside the patient body, i.e. the distal end, and the remaining part outside the body, e.g. the rear end, while enabling a fluid communication therebetween.

The term "automatic" is to be understood as self-propelled or moved without the intervention of a practitioner, e.g. by pushing.

The term "distal end portion" is to be understood as a zone substantially near the distal end and having a length of about 50% of the total length. In some examples, the distal end portion may be of about 10-60% of the total length. In some examples, the distal end portion may be of about 20% of the total length.

The term "expand" is to be understood as the deformation from a compact state to a wider shape and/or a greater diameter, e.g. as a result of an exerted pressure and/or a trigger. The terms "expand" and "deform" are herein used interchangeably.

The expression "device used with/by a single hand" is to be understood as a device which does not require more than one hand to be operated, that is, a device usable by a single practitioner without requiring both hands.

The term "corporal conduit" is to be understood as a human or animal natural anatomic cavity through which fluids such as air, blood, urine, bile, or cerebrospinal fluid etc., may flow. A corporal conduit may be elongated and hollow. The corporal conduit may be defined by walls. Examples of corporal conduit may comprise veins, trachea, urethra, arteries, oesophagus, etc.

The term "zone to be treated" is to be understood as a specific location of a corporal conduit or of a corporal cavity in which the distal end of the medical device is to be arranged. The terms "zone to be treated", "predetermined location", "target zone" and "required position" are interchangeably used herein.

The term "securely fixed" is to be understood as anchored or hold in a predetermined place, e.g. in the zone to be treated, and ready to start administering the required treatment. In an example, the anchoring may be implemented by a securing element such as an inflatable cuff. The inflatable cuff may be arranged at the outer side of the outer tube. In an example, the anchoring may be implemented by expanding the distal end portion of the outer tube.

The term "guiding position" is to be understood as a position of the medical device in which the medical device is configured to travel towards a predetermined location where the treatment is to be administered. In the guiding position, the outer tube is coupled to the inner guide for travelling together towards the target zone such that the internal cavity of the outer tube substantially fits the inner guide.

The term "operating position" is to be understood as a position of the device in which the inner guide has been removed from the outer tube so that the outer tube enables a fluid communication between an outside of the body to the target zone. The outer tube is thus ready to provide the required treatment e.g. providing mechanical ventilation to the patient while at the same time provides a transluminal access to the conduit, i.e. a fluid communication between the target zone and the outside of patient's body.

Figure 1B:
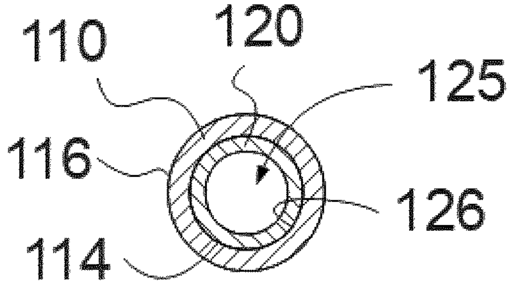
FIG. 1B schematically illustrates a medical device in the guiding position according to an example of the first aspect of the present disclosure.

FIGS. 1A and 1B schematically illustrate a medical device in the guiding position according to an example of the first aspect of the present disclosure. FIG. 1B is a cross-sectional view along the line A-A' of FIG. 1A.

The medical device 100 of these figures comprises an inner guide 120 and an outer tube 110. The inner guide 120 is inserted into an internal cavity 115 of the outer tube 110. The outer tube 110 extends from a rear end 113 to a distal end 112. The medical device 100 of these figures is travelling along a corporal conduit 20 to reach a target zone. The inner guide 120 and the outer tube are inserted together from an outside 22 of the patient's body. The external shape of the outer tube is smaller than the corporal conduit defined by a conduit wall 21. This smaller shape of the outer tube improves its insertion and movement inside the corporal conduit 20. Risk of injuring the patient may thus be reduced.

In these figures, the outer tube 110 comprises an inner surface 114 defining the cavity 115. The outer tube further comprises an outer surface 116. The outer tube 110 may thus outwardly extend from the inner surface 114 to the outer surface 116 defining an outer tube thickness.

In these figures, the inner guide 120 is a tube. The inner guide comprises an outer surface 126 and an internal passageway 125. The internal passageway 125 of these figures may be used for inputting and outputting fluids and/or drugs from inside the body's patient when the medical device is in the guiding position.

In these figures, the outer tube 110 engages with the inner guide 120. The internal cavity 115 of the outer tube 110 substantially fits the inner guide 120 for travelling together along the corporal conduit. In these figures, the inner surface 114 of the outer tube 110 contacts the outer surface 126 of the inner guide. In this example, the inner surface 114 of the outer tube 110 contacts the outer surface 126 along the whole perimeter. In some examples, a region of the inner surface 114 of the outer tube 100 may contact a region of the outer surface 126 of the inner guide 120.

In FIG. 1A, the inner guide comprises a distal end portion that protrudes a protruding length from the outer tube, e.g. from the distal end 112 of the outer tube. This protruding length may facilitate the insertion of the outer tube inside the corporal conduit. In some examples, the cross section of the inner guide decreases along the protruding length so as to further facilitate guiding the outer tube along the corporal conduit.

In some examples, the inner guide comprises a bendable portion, e.g. of about 5-10 cm, arranged at the protruding length of the distal end portion. The bendable portion may thus enter before the outer tube inside the corporate conduit. Guidance of the outer portion may thus be further enhanced.

The inner guide 120 may comprise a plurality of cables (not shown) to move the bendable portion to a required angle. In an example, the angular range of the bendable portion may be of about 60°-180°, e.g. 120°. In an example, the bendable portion may be the distal end portion. In another example, the bendable portion may be part of the distal end portion.

In some examples, the protruding length may be configured to create a conduit through body tissues. For example, the protruding length of the inner guide may comprise a cutting element to cut body tissues for reaching the target zone. This cutting element may thus be used for making incisions for creating a passageway from an outside of the body towards the target zone inside the body. This cutting element may be rigid and sharpened in order to facilitate the insertion and/or the navigation of the device through the tissues.

The inner guide 120 may be made of any medically suitable material, e.g. polyvinylchloride (PVC) or silicone, a blend or combination thereof, etc. In an example, the bendable portion may comprise an additional material to be more flexible than the remaining portion of the inner guide 120.

The outer diameter of the inner guide may be of about 0.5-20 mm. The outer diameter may depend on the application. For example, an outer diameter between 2-9 mm may be used in an endotracheal intubation. In other examples, the outer diameter may be of about 0.5-3 mm, for example for accessing a vein in paediatrics may be about 0.5 mm. For, a thoracic trocar may involve diameters between 15-20 mm.

In some examples, the inner guide 120 may also comprise a pressure-exerting element which may be configured to exert pressure outwardly. The pressure-exerting element may be a separate element which may be arranged in the inner guide. The pressure-exerting element may be arranged at the outer surface of the inner guide 120 and may extend longitudinally along at least a portion of inner guide. The pressure-exerting element may be made of an expansible material which facilitates the deployment and the retraction, i.e. the unfolding, of the pressure-exerting element repeatedly, e.g. polyvinylchloride (PVC), silicones or polyurethane.

Depending on the deployment degree, the pressure-exerting element may comprise at least two different states: an un-deployed state in which the pressure element is folded and/or does not exert any pressure, and a deployed state in which the pressure element is un-folded and exerts a predetermined pressure. In an example, the pressure-exerting element may also comprise a partially deployed state in which the pressure element is partially un-folded and/or exerts less pressure than in the deployed state.

In some examples, the pressure-exerting element may be fluid-inflatable, e.g. by (hot) air or (hot) water, and may comprise an inflating lumen to input and output the fluid in order to regulate the deployment. The pressure-exerting element may be made of a material that allows transmission of a trigger to the outer tube.

In an example, the inner guide according to any of the disclosed examples may further comprise a visualization system, e.g. an illuminating element, e.g. a led, and/or a camera, to enable direct visualization.

Figure 2A:
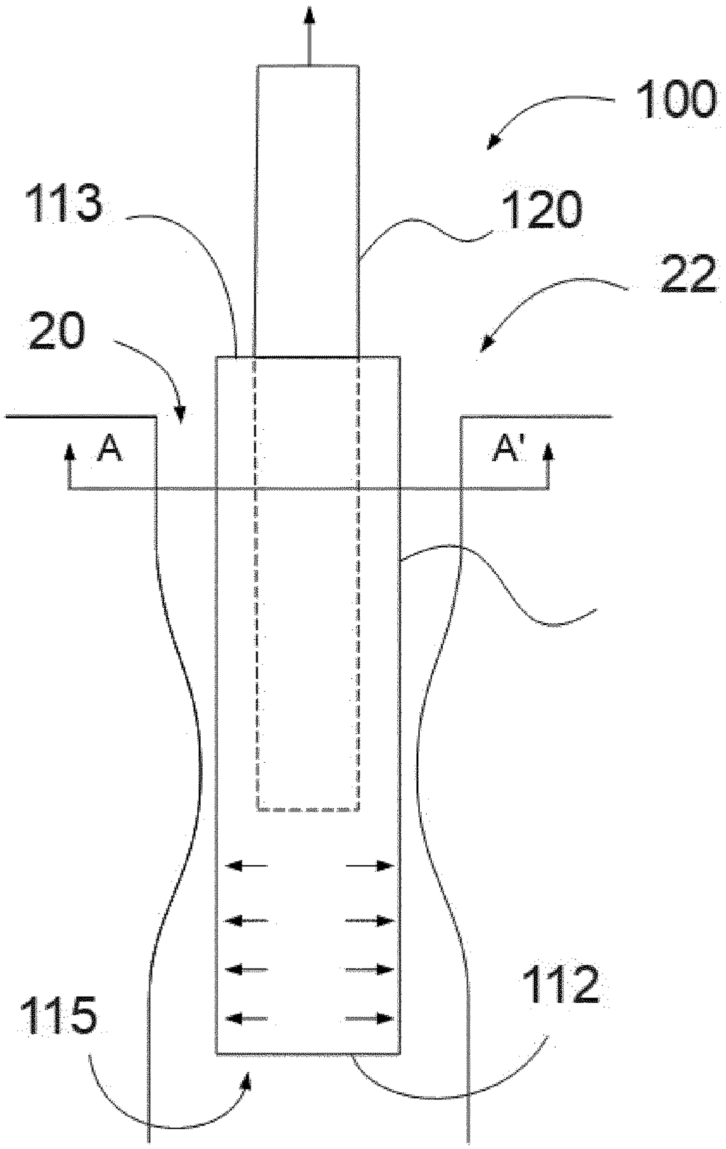
FIG. 2A schematically illustrates a medical device being shifting from the guiding position to the operating position according to an example of the first aspect of the present disclosure.
Figure 2B:
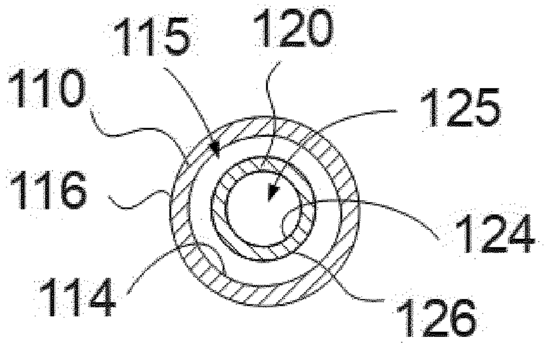
FIG. 2B schematically illustrates a medical device being shifting from the guiding position to the operating position according to an example of the first aspect of the present disclosure.

FIGS. 2A and 2B schematically illustrate a medical device 100 being shifting from the guiding position to the operating position according to an example of the first aspect of the present disclosure. In these figures, the distal end 112 of the outer tube is placed on the target zone. The inner guide 120 of these figures has been disengaged from the outer tube 110 and is being removed from the internal cavity 115.

As depicted in FIG. 2A, the rear end 113 of the outer tube is outside 22 the patient's body, whereas the distal end 112 is inside the patient's body, e.g. corporal conduit 20.

Comparing the FIGS. 2A-2B to FIGS. 1A-1B, the shape of the internal cavity 115 has changed. In FIGS. 2A-2B, the inner diameter of the internal cavity 115 has increased. The outer diameter of the outer tube 110 defined by the outer surface 116 has also increased. In these figures, the outer tube 110 has uniformly expanded in response of a trigger, e.g. transmitted by the inner guide 120 or by conditions inside the corporal conduit 20.

The outer guide may comprise a shape-memory material. In FIGS. 1A-1B, the outer guide 110 may be in a deformed shape and in FIGS. 2A-2B in the original shape.

Figure 3A:
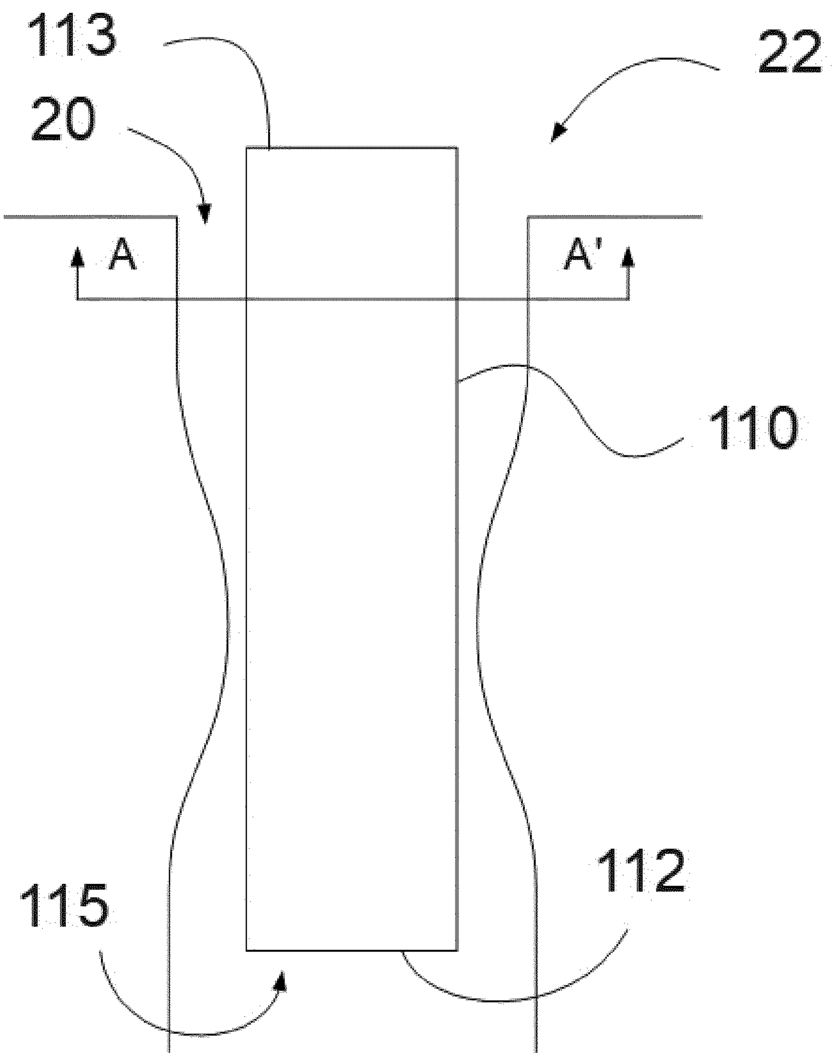
FIG. 3A schematically illustrates a medical device in the operating position according to an example of the first aspect of the present disclosure.
Figure 3B:
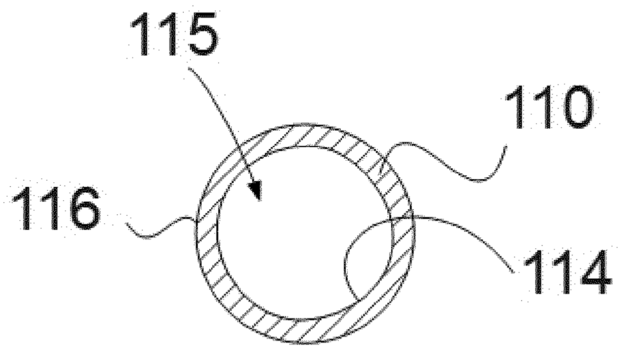
FIG. 3B schematically illustrates a medical device in the operating position according to an example of the first aspect of the present disclosure.

FIGS. 3A and 3B schematically illustrate a medical device in the operating position according to an example of the first aspect of the present disclosure. In these figures, the inner guide has been completely removed from the outer tube 110. A transluminal access is thus created by the internal cavity 115 from the rear end 113 outside the corporal conduit to the distal end 114 inside the corporal conduit. A fluid communication between the target zone and the outside of the body is thus established.

As depicted in FIGS. 3A and 3B a gap is formed between the outer tube 110 and the corporal conduit 20. In an example, the outer tube may comprise a securing element (not shown) for securely fixing the outer tube to the corporal conduit. Such securing element may comprise two different states: an undeployed state in which the securing element is folded; and a deployed state in which the securing element is un-folded and exerts a pressure, e.g. against the walls of a corporal conduit so as to secure the outer tube therein and/or seal the conduit entirely to prevent fluids from entering thereinto.

In an example, the securing element may be an inflatable cuff. In an example, the securing element may be fluid-inflatable, e.g. by air or water, and may comprise an inflating lumen to input and output the fluid in order to regulate the deployment state.

In an example, the outer tube may be an endotracheal tube. In other examples, the outer tube may be a catheter providing transluminal access in a corporal conduit, e.g. in a vein or in the urethra.

FIGS. 4A-4D schematically illustrate several examples of an inner guide according to the first aspect of the present disclosure. The inner guide of these figures may comprise a shape-memory material.

Figure 4A:
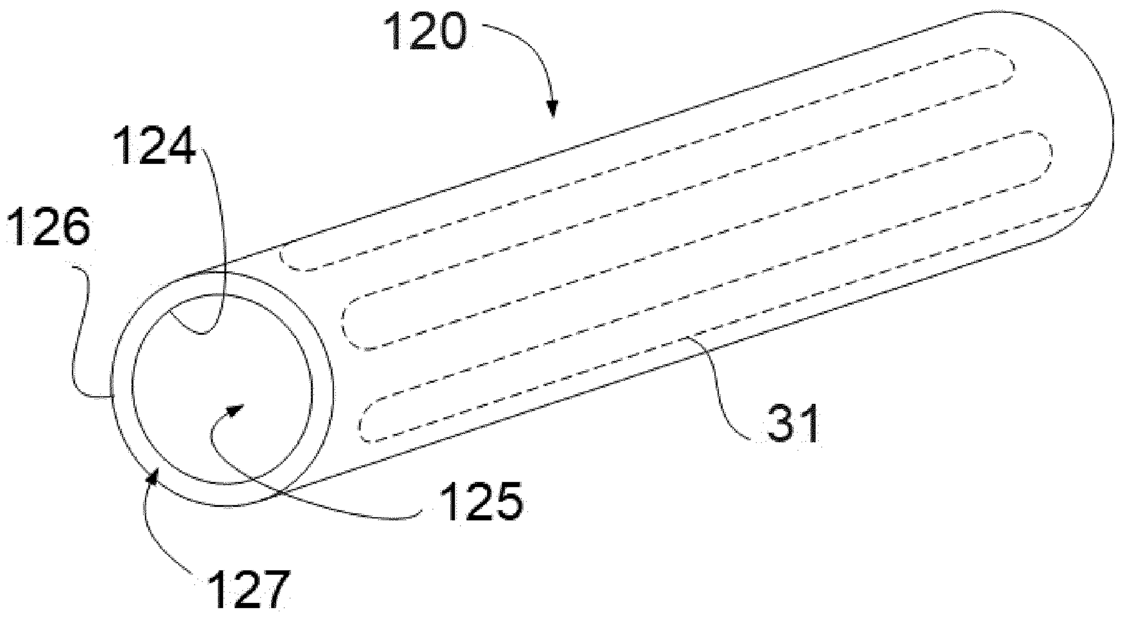
FIG. 4A schematically illustrates an example of an inner guide according to the first aspect of the present disclosure.

FIG. 4A illustrates an inner guide 120 comprising an electrical resistance 31 embedded in the wall 127 of the inner guide. The wall 127 is defined between the inner surface 124 and the outer surface 126. In this figure, the inner guide 120 also comprises an internal passageway for inputting and outputting fluids and/or drugs when the medical device is in the guiding position.

The electrical resistance 31 may be heated by Joule effect. Two ends of the electrical resistance may be connected to an electrical source to generate an electrical current that produces heat. This heat may thus be transferred to outer tube. In this example, the electrical resistance 31 runs through the wall 127 in a zig-zag manner. However, in other examples, the electrical resistance may be arranged in other suitable manners, e.g. in a spiral-like manner. In some examples, a plurality of electrical resistances may be arranged through the wall following an axial direction.

In some examples, the internal cavity of the outer tube may match the outer surface 126 of the inner surface when no electric current flows through the electrical resistance 31. By creating an electric current through the electrical resistance, the inner guide may be heated and the cavity of the outer tube may change its shape in response of this temperature increase.

Figure 4B:
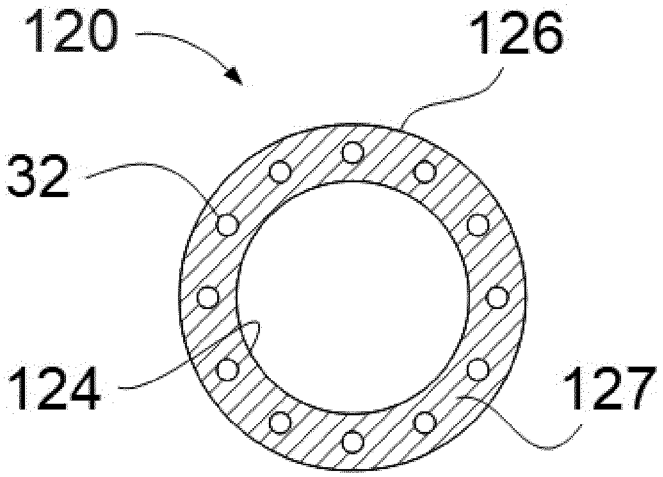
FIG. 4B schematically illustrates an example of an inner guide according to the first aspect of the present disclosure.

FIG. 4B illustrates a cross-sectional view of an inner guide 120 comprising a plurality of axially extending thermal fluid paths 32. The thermal fluid paths 32 are arranged within the wall 127 defined between the outer surface 126 and the inner surface 124. A heated or a cooled fluid may thus circulate through the thermal fluid paths. The thermal fluid may thus cool or heat the inner guide, and consequently, the outer tube when placed around the inner guide.

Figure 4C:
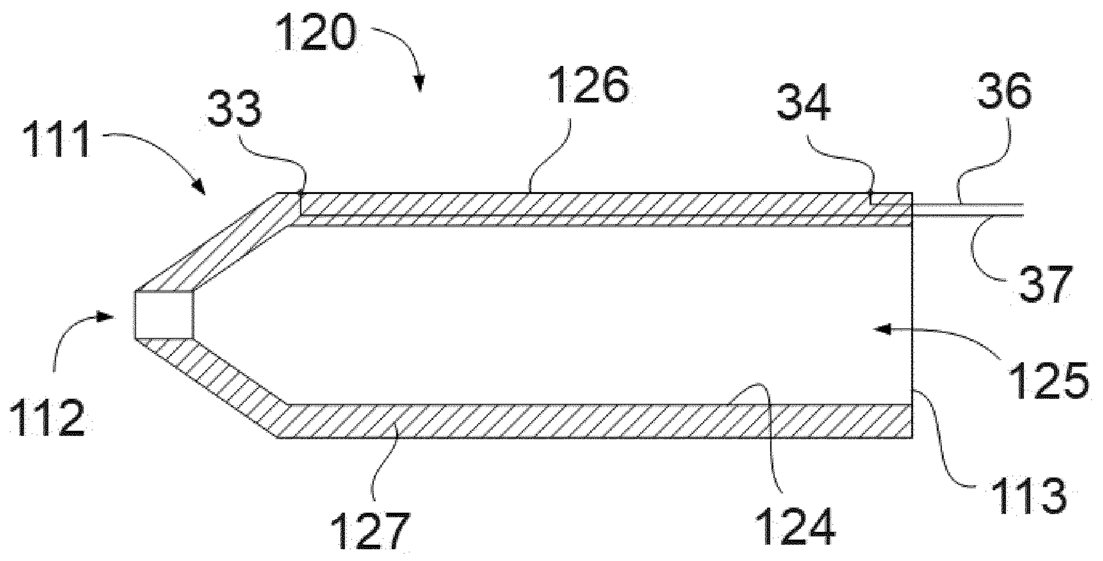
FIG. 4C schematically illustrates an example of an inner guide according to the first aspect of the present disclosure.

FIG. 4C illustrates a cross-sectional view of an inner guide 120 comprising a pair of electrically conductive elements 33, 34 to be in contact with an inner surface of the outer tube. The electrically conductive elements 33, 34 may slightly protrude in a radial direction from the outer surface 126 of the inner guide 120. An electrical wire 35 is connected to the electrically conductive element 33 and an electrical wire 36 to the electrically conductive element 34. These electrical wires 35 and 36 are connected to an electrical source (not shown in FIG. 4C) to generate a voltage difference between the electrical conductive elements 33 and 34. The electrical conductive elements 33 and 34 may act as electrodes inducing an electrical current through the outer tuber when the outer tube is in contact with these electrical conductive elements 33 and 34. In some examples, the inner guide may comprise a plurality of pair of electrical conductive elements according to any of the examples herein disclosed. In this figure, the electrically conductive element 33 is adjacent to the distal end 112 and the conductive element 34 adjacent to the rear end 113 of the inner guide.

In this example, the electrical wires 35 and 36 are arranged within the wall 127, however in other examples the electrical wires may be arranged in a dedicated tube inside the passageway 125.

The inner guide 110 of this figure comprises a distal end portion 111 adjacent to the distal end 112. The cross-section of the distal end portion increases from the distal end 112 towards the rear end 113. In this example, the distal end portion forms a gradually increasing gradient diameter from the distal end.

By having a gradually increasing diameter gradient at the inner guide, the outer tube (and thus the whole medical device) may be more easily introduced and guided through a corporal conduit which reduces the risk of injuring the patient internally. Furthermore, the outer tube may be more precisely placed in the zone to be treated or target zone.

Figure 4D:
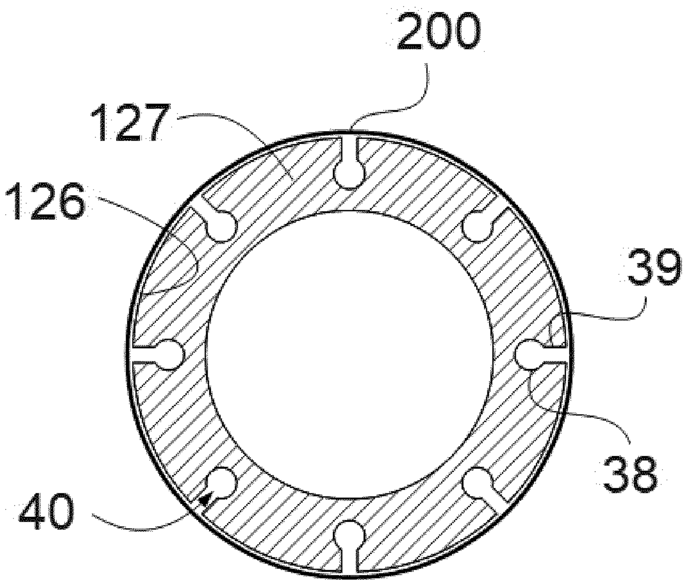
FIG. 4D schematically illustrates an example of an inner guide according to the first aspect of the present disclosure.

FIG. 4D illustrates a cross-sectional view of a pressure exerting element 200 placed around the inner guide 120. In this figure, the pressure exerting element 200 is a deformable layer arranged on the outer surface 126 of the wall 127 of the inner guide 120. A pressure fluid may be directed towards the pressure exerting element 200 for outwardly deforming. This deformation may exert a pressure on the outer tube. When the medical device in in the guiding position, the pressure exerting element 200 may be clamped between the internal cavity of the outer tube and the outer surface 126 of the inner guide.

In this figure, the wall 127 comprises a plurality of fluid pressure channels 38 extending from the rear to the distal end of the inner guide. The outer surface 126 comprises a plurality of orifices 40 for guiding a fluid pressure against the pressure exerting element 200. Conduits 39 may connect the fluid pressure channels 38 to the orifices 40. The fluid pressure may thus be homogenously directed towards the pressure exerting element to cause a substantially uniformly deformation.

In some examples, the pressure exerting element may be heated, e.g. electric current or a heated fluid flowing. The pressure exerted by the pressure exerting element may be combined with heat to trigger the change of the shape of the outer tube. For example, the pressure fluid flowing through the fluid pressure channels 38 may be heated.

In some examples, the inner diameter of the outer tube may be 1-2 mm greater that the outer diameter of the internal guide when the medical device is in the guiding position. When the internal guide transmits the trigger through the pressure exerting element, the outer tube may recover an original diameter greater than the diameter at the guiding position. In such examples, prior to the expansion, the pressure-exerting element may contact both the inner guide and the outer tube thereby facilitating the transmission of heat or an electrical current from the inner guide to the outer tube.

The pressure-exerting element may according to any of the examples of pressure-exerting elements described in connection to the examples of the second aspect of this disclosure.

Figure 5:
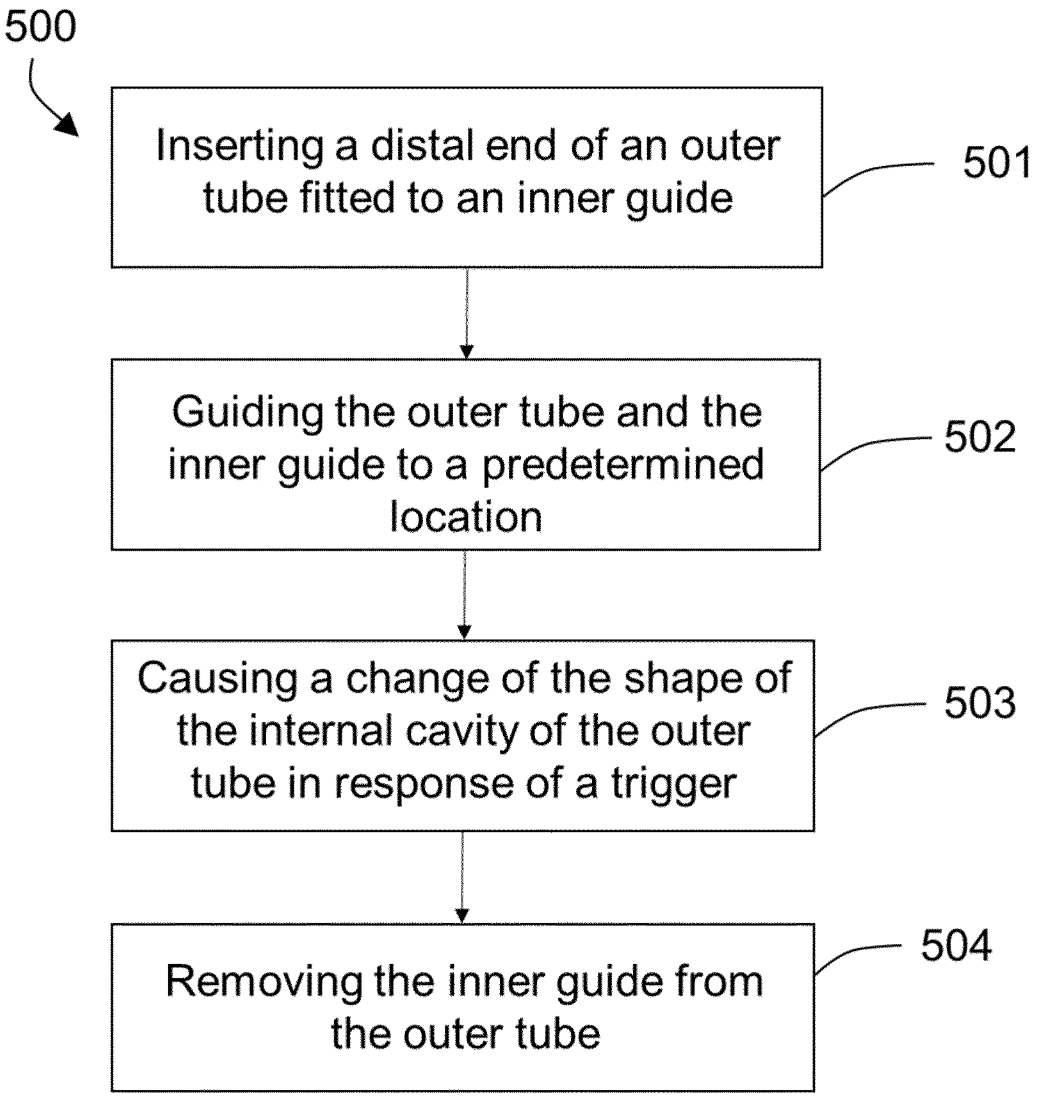
FIG. 5 illustrates a flow chart of a method for arranging a transluminal medical device in a patient's body according to an example of the first aspect of the present disclosure.

FIG. 5 illustrates a flow chart of a method 500 for arranging a transluminal medical device inside a patient's body to reach a target zone according to an example of the first aspect of the present disclosure.

The method comprises inserting a distal end of an outer tube fitted to an inner guide into a patient's body as represented at block 501. The outer tube and the inner guide are thus inserted together. The outer tube and the inner guide may be inserted into the patient's body through a corporal conduit or through tissues with an incision. Prior to inserting the medical device, the outer tube is placed around the inner guide. A cavity of the outer tube may receive the inner guide. The outer tube may be connected to the inner guide.

For example, when the outer tube comprises a shape-memory material, a stimulus may be applied to the outer tube to change its shape for engaging the inner guide. The internal cavity of the outer tube may thus be compressed for fitting the inner guide. In some examples, the stimulus may be applied during the insertion to maintain the outer tube in its deformed shape. For example, an electrical current may be applied to the outer tube during guiding inside the patient's body to reach the target zone, e.g. a corporal conduit, to maintain the outer tube in a deformed shape.

The method 500 further comprises guiding the outer tube and the inner guide to a predetermined position inside the patient's body to reach the target zone as represented at block 502. The outer tube and the inner guide may reach the target zone by travelling along corporal conduits and/or through body tissues. In some examples, guiding the outer tube and the inner guide may comprises operating a bendable portion of the inner guide.

In addition, the method 500 comprises causing a change of the shape of the internal cavity of the outer tube in response of a trigger as represented at block 503. When the outer tube has reached the target zone a trigger may be applied for causing a change of the shape of the internal cavity of the outer tube. The trigger may be according to any of the examples herein disclosed.

In some examples, the change of the shape may be triggered by a change in temperature and/or pH experienced by the outer tube when reaches the target zone.

In some examples, the trigger may be transmitted by the inner guide. A trigger actuator may be operated to transmit the trigger through the inner guide towards the outer tube.

In some examples, transmitting a trigger may comprise stopping to apply a stimulus on the outer tube. For example, stopping to apply an electrical current to the outer tube. In the absence of an electrical current, the outer tube may recover its original shape.

The method 500 further comprises removing the inner guide from the outer tube as represented at block 504. The change of the internal cavity of the outer tube caused by the trigger allows removing the inner guide. The internal cavity of the outer tube thus establishes a fluid communication between the target zone and the outside of the body, e.g. a transluminal access to a corporal conduit, according to any of the examples herein disclosed. A treatment, e.g. mechanical ventilation, may be administered through the outer tube.

FIG. 6 shows an exploited view of a medical device 100 according to an example of the second aspect of the present disclosure. For a better understanding, the proportions in FIGS. 6, 7A and 7B are not in scale. The medical device 100 may comprise an outer tube 110 and an inner guide 120, and may enable a communication between an inside and an outside of the body, e.g. transluminal access to a corporal conduit. The outer tube 110 extends from a rear end 113 to a distal end 112.

The inner guide 120 may comprise a distal end portion 121, i.e. a zone comprising about 1-50% of the total length of the inner guide. In some examples, the distal end portion may be of about 10-60% of the total length. In some examples, the distal end portion may be of about 20% of the total length. The distal end portion 121 may be adjacent to the distal end 112 of the inner guide.

The inner guide 120 may also comprise a bendable portion, e.g. of about 5-10 cm, to facilitate the navigation of the device through sinuous conduits from the insertion point to the zone to be treated, e.g. through existing corporal conduits or through conduits created for reaching the target zone. In an example, the distal end portion of the inner guide may comprise the bendable portion.

The inner guide 120 may comprise a plurality of cables (not shown) to move the bendable portion to a required angle. In an example, the angular range of the bendable portion may be of about 60°-180°, e.g. 120°. In an example, the bendable portion may be the distal end portion 121. In another example, the bendable portion may be part of the distal end portion 121.

Alternatively, the distal end portion may be rigid and sharpened in order to facilitate the insertion and/or the navigation of the device through the tissues.

The inner guide 120 may be made of any medically suitable material, e.g. polyvinylchloride (PVC) or silicone, a blend or combination thereof, etc. In an example, the bendable portion may comprise an additional material to be more flexible than the remaining portion of the inner guide 120.

In some examples, the inner guide may be expandable. The inner guide may be similar to the outer tube according to any of examples herein disclosed. In such examples, the material of the inner guide may be any material that enables the expansion of the inner guide.

The inner guide 120 may comprise an outer diameter narrow enough to facilitate the insertion and the navigation through a corporal conduit thereby reducing the risk of injuring the patient internally. The outer diameter of the inner guide may vary according to the corporal conduit in which the medical device to be inserted. In an example, the outer diameter may be of about 2-9 mm. These outer diameters may be used in an endotracheal intubation. In another example, the outer diameter may be of about 0.5-3 mm.

The inner guide 120 may comprise an internal passageway (not shown) to allow fluids such as air to flow bidirectionally, i.e. in and out the conduit. In an example, the internal passageway may firstly provide an oxygen supply and subsequently a suction force.

As shown in FIG. 6, the inner guide 120 may also comprise a pressure-exerting element 200 which may be configured to exert pressure outwardly. In an example, the pressure-exerting element may be a separate element which may be arranged in the inner guide. The pressure-exerting element 200 may be arranged at the outer wall of the inner guide 120 and may extend longitudinally along at least a portion of the distal end portion 121. The pressure-exerting element 200 may be made of an expansible material which facilitates the deployment and the retraction, i.e. the unfolding, of the pressure-exerting element repeatedly, e.g. polyvinylchloride (PVC), silicones or polyurethane.

Depending on the deployment degree, the pressure-exerting element 200 may comprise at least two different states: a un-deployed state in which the pressure element is folded and/or does not exert any pressure, and a deployed state in which the pressure element is un-folded and exerts a predetermined pressure. In an example, the pressure-exerting element may also comprise a partially deployed state in which the pressure element is partially un-folded and/or exerts less pressure than in the deployed state.

In an example, the pressure-exerting element 200 may be an inflatable cuff. In an example, the pressure-exerting element 200 may be fluid-inflatable, e.g. by (hot) air or (hot) water, and may comprise an inflating lumen to input and output the fluid in order to regulate the deployment. The pressure-exerting element 200 may be made of a material that allows transmission of a trigger to the outer tube. The trigger may be triggered from either the pressure element, e.g. if inflated by a heated fluid, or from the inner guide, e.g. if a heated fluid flows through an inner lumen or passageway.

In an example, the inner guide according to any of the disclosed examples may further comprise a visualization system, e.g. an illuminating element, e.g. a led, and/or a camera, to enable direct visualization.

As shown in FIG. 6, the medical device 100 may also comprise an outer tube 110.

The outer tube 110 may comprise an inner passageway (not shown) to receive the inner guide 120, as shown in, e.g. FIG. 7A. The diameter of the outer tube may be bigger, i.e. of about 5-50%, than the diameter of the inner guide to enable the insertion of the inner guide therein. In addition, the diameter of the outer tube may, in the guiding position, provide enough space for at least partially deploying the pressure-exerting element. Therefore, when the inner guide 120 is inserted into the outer tube, the overall outer diameter of the medical device 100 may substantially correspond to the diameter of the inner guide thereby facilitating the insertion into a corporal conduit and also the navigation therethrough.

The outer tube 110 may comprise a distal end portion 111 which may be of about 1-50% of the total length of the outer tube. In an example, the distal end portion 111 may be of about 10-20% of the total length of the outer tube. In an example, the distal end portion may have a length of about 1-30 cm. In some examples, the distal end portion of the outer tube may be configured to be expanded after receiving a trigger e.g. electric current or heat, or any other suitable trigger. Alternatively, or additionally, the distal end portion may also be expanded upon exertion of a pressure. In an example, the whole outer tube may be expandable.

In an example, the outer tube may comprise a securing element (not shown) for securely fixing the outer tube to a corporal conduit. Such securing element may comprise two different states: an undeployed state in which the securing element is folded; and a deployed state in which the securing element is un-folded and exerts a pressure, e.g. against the walls of a corporal conduit so as to secure the outer tube therein and/or seal the conduit entirely to prevent fluids from entering thereinto.

In an example, the securing element may be an inflatable cuff. In an example, the securing element may be fluid-inflatable, e.g. by air or water, and may comprise an inflating lumen to input and output the fluid in order to regulate the deployment state.

In an example, the outer tube may be an endotracheal tube. In other examples, the outer tube may be a catheter providing transluminal access in a corporal conduit, e.g. in a vein or in the urethra.

FIG. 7A depicts a medical device 100 having the inner guide within the outer tube. The pressure-exerting element of the inner guide, in undeployed state, may be arranged substantially corresponding with the distal tip of the outer tube to facilitate a subsequent releasable anchoring between the inner guide and the outer tube. In an example, the inner guide may be arranged to slightly protrude a length from the outer tube. In an example, the bendable portion of the inner guide protrudes from the outer tube 4-5 cm. In another example, the distal tip of the inner guide may be rigid i.e. not bendable, and may be the portion protruding a length from the outer tube.

FIG. 7B depicts a medical device 100 in the guiding position of an example wherein the device has a diameter gradient i.e. the diameter of the outer tube is substantially greater the outer diameter of the inner guide outer diameter. FIG. 7B also depicts the pressure-exerting element 200 in a deployed state, thereby comprising a progressively increasing diameter gradient 130. Such progressive diameter change facilitates both the insertion and navigation of the medical device, thereby reducing the risk of injuring the patient.

Depending on the configuration, the medical device 100 may have at least two different positions: a guiding position and an operating position.

In order to set the medical device into the guiding position, the inner guide may be arranged within the outer tube (see FIG. 7A). In an example, a length of the pressure-exerting element may be arranged out of the outer tube.

At the guiding position, the pressure-exerting element may be partially deployed thereby releasably coupling inner guide and outer tube together. The pressure-exerting element may exert a pressure against the inner walls of the outer tuber, which generates a frictional force to releasably engage with the pressure-exerting element. As a result, both elements may be introduced and guided together easily through the corporal conduit. The pressure-exerting element may be attached, e.g. glued, to the inner guide or be integral part.

In addition, in FIG. 7B, the pressure-exerting element enables a progressive transition from the outer diameter of the inner guide to the outer diameter of the outer tube, which reduces the change of diameter smoothly. Such progressively increasing diameter gradient further facilitates the introduction of the medical device 100 into the corporal conduit and also the navigation through the corporal conduit, e.g. by reducing the probabilities to hit the vocal cords.

At operating position (not shown), the inner guide may be removed from the outer tube, e.g. by folding the pressure-exerting element to the undeployed state. The inner passageway of the outer tube may, therefore, be un-occluded for administering the required treatment, e.g. enabling mechanical ventilation of the patient. Additionally, the outer tube 110 may be securely fixed to the corporal conduit, e.g. by deploying a securing element.

In an example, the distal end portion of the outer tube may be made of or may comprise a material that enables at least the distal end portion to expand and/or deform upon exertion of a pressure or upon being triggered thereby providing an outer tube with the same diameter i.e. the diameter of the distal end portion diameter and of the remaining portion of the outer tube may then be equalized. In an example, the outer tube may be made of a material that enables the whole outer tube to be expanded.

The expansion of a distal end portion may provide an outer tube with an internal passageway that enables a fluid flow into the conduit. In addition, the outer tube may comprise a securing element e.g. an inflatable cuff, to securely fix the outer tube to de corporal conduit and may also prevent undesired fluids from entering into the conduit.

The expanded shape of the outer tube may depend on the pressure-exerting element e.g. the maximum deployment, the arrangement, the length, etc. In an example, the pressure-exerting element may comprise a length equal or substantially similar to the length of the expandable portion of the outer tube.

In some examples, the whole outer tube may be expandable which may provide a compact medical device which may further facilitate the insertion and/or navigation of the device in a corporal conduit. In such examples, the pressure-exerting element and the outer tube may comprise the same length, i.e. to enable the expansion of the whole outer tube.

The distal end portion of the outer tube 111 or the whole outer tube may be made of a shape-memory material, e.g. PLC-PLLA, Polyurethanes or similar. The shape-memory material may enable reducing the diameter of the outer tube (compared to a predefined diameter) before being inserted into a corporal conduit which facilitates the insertion of the medical device. Upon receiving a trigger, e.g. heat, electricity, a pH change or similar or any combination thereof, from the pressure-exerting element, the outer tube may recover a predefined diameter or shape. The pressure-exerting element may also contribute to accelerate the conformational change expanding the tube by exerting further pressure. In an example, the expansion may be triggered by heat and may be enhanced or promoted by the pressure exerted by the pressure-exerting element. Being able to set the outer tube in a compact or reduced state during the insertion and navigation enables reducing the overall outer diameter of the medical device which facilitates both the insertion and the navigation through a corporal conduit.

In examples comprising an outer tube having an expandable distal end portion, the medical device 100 may have at least three different positions depending on the configuration of the outer tube: a guiding position, an expanding position and an operating position.

The guiding position (see FIG. 7B), the pressure-exerting element may be (partially) deployed and/or may exert a minimum pressure to releasably couple the inner guide with the outer tube and also to prevent the distal end portion of the outer tube from being expanded. In the expanding position (see FIG. 6A) the pressure-exerting element may progressively expand and therefore, gradually increase the exerted pressure, as a result the outer tube may gradually expand or may transmit a trigger to the outer tube thereby triggering the expansion of the outer tube. At operating position (see FIG. 6B), the outer tube may be securely fixed to the corporal conduit and the inner guide may be removed from the outer tube after setting the pressure-exerting element in the undeployed state. The internal cavity of the outer tube may therefore be left un-occluded for administering the required treatment, e.g. enabling mechanical ventilation of the patient.

The medical device 100 may further comprise a control casing. In some examples, the control casing may comprise at least a fluid inputting port, a fluid outputting port, a plurality of actuators and a gripping area. The control casing may be according to any of the examples herein disclosed.

Figure 8:
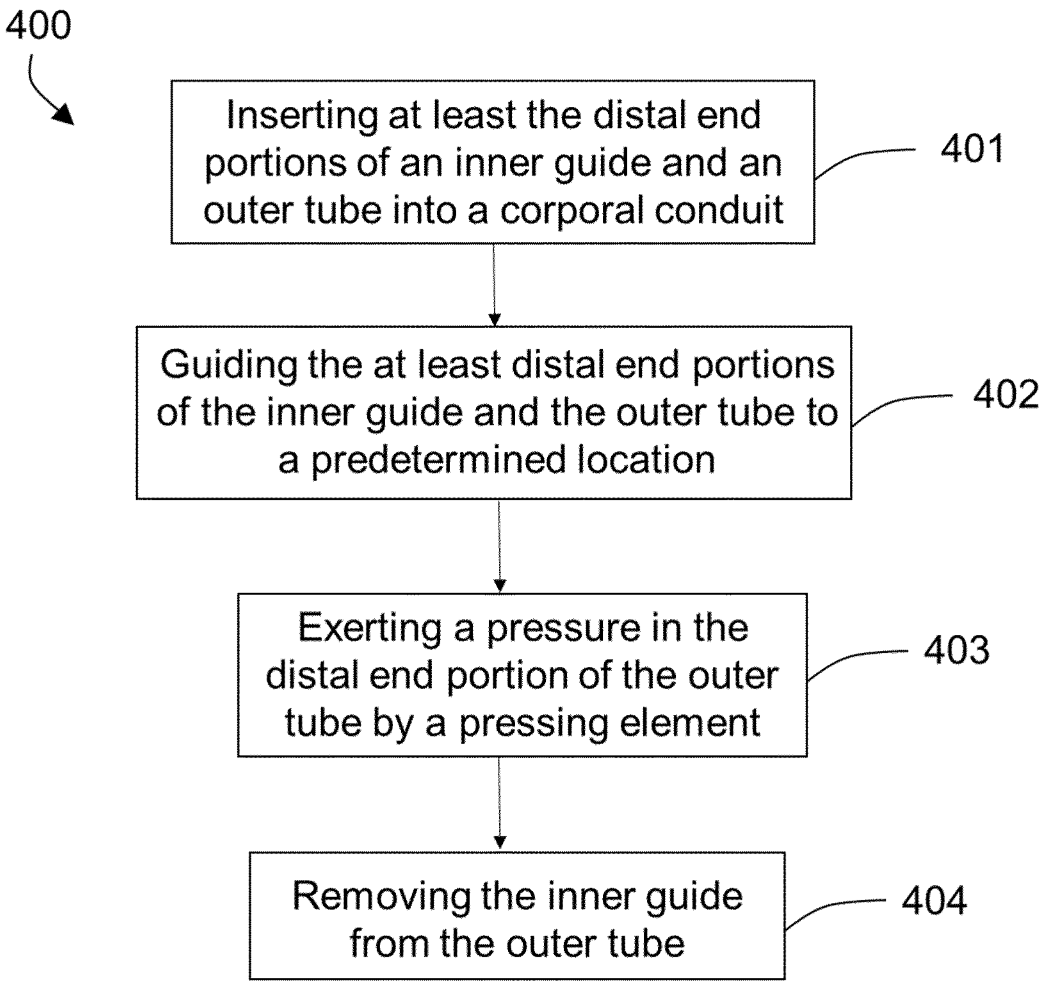
FIG. 8 illustrates a flow chart of a method for arranging a transluminal medical device in a patient's body according to an example of the second aspect of the present disclosure.

FIG. 8 depicts a flow chart of a method 400 for arranging a transluminal medical device in a corporal conduit. Firstly, an inner guide comprising a distal end portion and a pressure element; and an outer tube comprising a distal end portion may be provided. The inner guide may further comprise a bendable portion or a cutting element and an internal passageway for the flow of fluids. In an example, the bendable portion or the cutting element may be arranged at the distal end portion. In an example, a control casing may also be provided.

At least the distal end portion of the inner guide may, in block 401, be inserted within or into the distal end portion of the outer tube. The inner guide and the outer may, in block 402, be releasably coupled e.g. by partially deploying the tube pressure-exerting element thereby setting the medical device into the guiding position (see e.g. FIG. 7B). In an example, the inner guide may be arranged to protrude a length from the outer tube.

The proximal portions of the inner guide and the outer tube may be coupled to the control casing. In some examples, the outer tube may be only releasably coupled to the inner guide via the pressure-exerting element i.e. it may not be coupled to the control casing. Then, at least the distal end portions of the inner guide and the outer tube may, in block 403, be inserted together into a corporal conduit. The distal end portions of inner guide and the outer tube may, in block 404, be guided to a predetermined location i.e. the zone to be treated or the target zone. If required, in examples wherein the inner guide comprises a bendable portion, the bendable portion may be bent, e.g. by actuating a bending actuator, in order to facilitate the navigation of the inner guide, and thus, of the whole medical device, through sinuous conduits.

After placing the distal end portions in place, i.e. at the zone to be treated, the inner guide may, in block 405, be removed from the outer tube after folding the pressure-exerting element to the undeployed state thereby setting the medical device in the operating position. Additionally, the outer tube may be decoupled from the control casing, e.g. actuating a locking actuator. Once in the operating position, only part of the outer tube, e.g. the distal end portion, may remain within the corporal conduit thereby obtaining a transluminal access. At the operating position, the treatment, e.g. mechanical ventilation, may be administered.

In an example, and prior to remove the inner guide, the outer tube may be securely fixed or anchored to the corporal conduit e.g. by deploying a securing element arranged at the outer wall of the outer tube.

In cases wherein at least the distal end portion of the outer tube is made of a shape-memory material, once the distal end portions of the inner guide and the outer tube are in place and before removing the inner guide from the outer tube, the method 400 may further comprise, in block 405, expanding at least the distal end portion of the outer tube. In some examples, the whole outer tube may be expanded. The expansion may be triggered e.g. by the heat from a heated fluid or by electric current. The heat and/or the electric current may be transferred from the pressure-exerting element to the outer tube, wherein the pressure element may be connected to the control casing which may generate the trigger. In some examples, the heat or the electric current may be transferred from the inner guide to the outer tube via the pressure-exerting element. At least the distal end portion of the outer tube may be expanded e.g. until the predefined diameter or shape. In some examples, the predefined diameter of the distal end zone may correspond to the diameter of the remaining portion of the outer tube.

Figure 9:
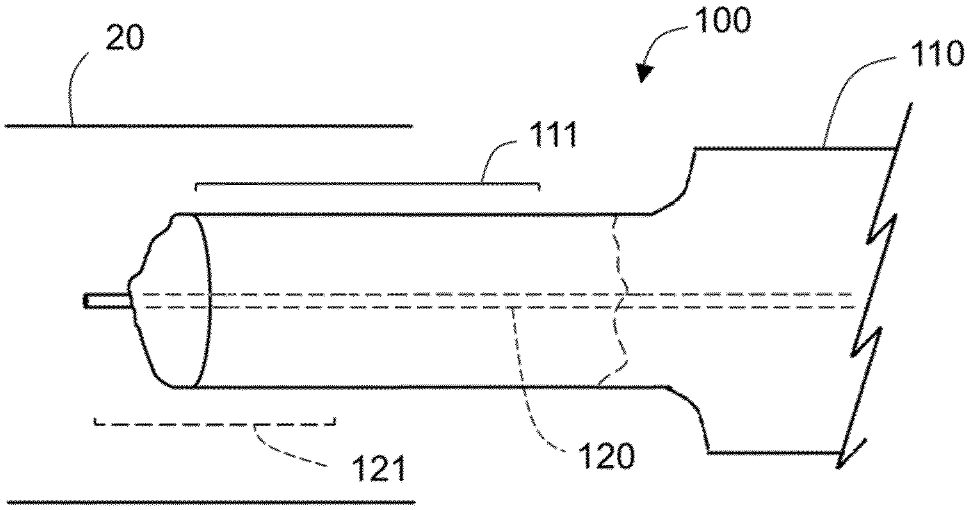
FIG. 9 schematically illustrates a medical device according to an example of the second aspect of the present disclosure at a guiding position.

FIG. 9 depicts the distal end portion a medical device 100, i.e. the portion comprising at least the distal end portions 111, 121 of in the inner guide 120 and outer tube 10, respectively; after being inserted into a corporal conduit. In the figure, the medical device 100 is shown in the guiding position i.e. having the pressure-exerting element partially deployed thereby removably coupling the inner guide and the outer tube.

Figure 10A:
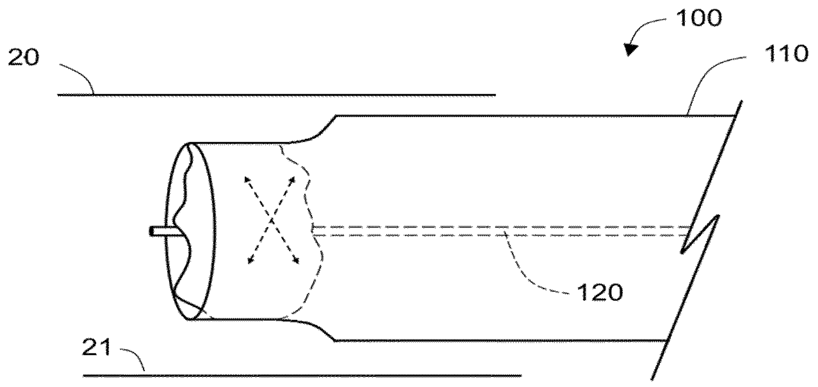
FIG. 10A schematically illustrates a medical device according to an example of the second aspect of the present disclosure in a corporal conduit.
Figure 10B:
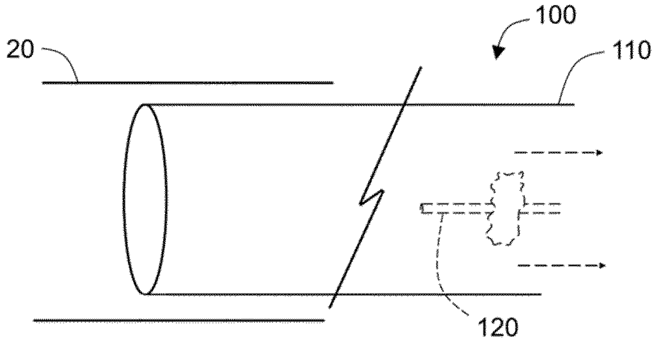
FIG. 10B schematically illustrates a medical device according to an example of the second aspect of the present disclosure at an operating position.

FIGS. 10A and 10B depict a medical device 100 having an outer tube with an expandable distal end, the medical device being placed in the required position. FIG. 10A depicts a medical device 100 with the pressure-exerting element being progressively deployed e.g. by actuating a pressing actuator. As the pressure-exerting element is deployed, its volume and the pressure exerted against the outer tube (see the arrows) increase thereby deforming the distal end portion 111.

FIG. 10B shows the medical device 100 almost in the operating position i.e. as the inner guide is being removed from the outer tube. The figure shows the medical device 100 having the distal end portion of the outer tube expanded thereby avoiding undesired fluids to enter into the conduit and also a secure fixation of the tube inside the conduit.

Figure 11:
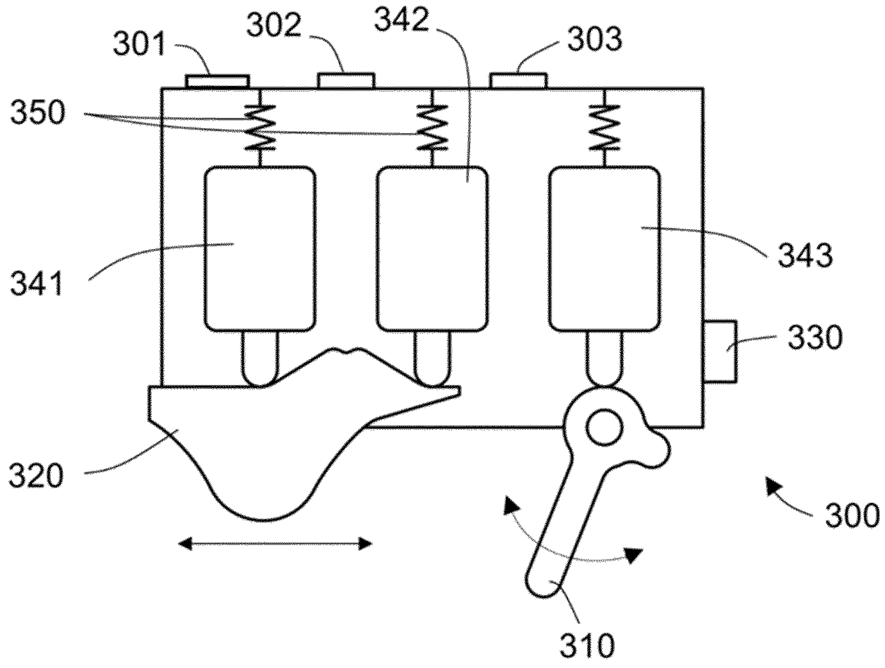
FIG. 11 schematically illustrates a control casing according to an example of the first and/or the second aspect of the present disclosure.

FIG. 11 schematically illustrates a control casing according to an example of the first and/or the second aspect of the present disclosure. The control casing 300 of this figure comprises a plurality of actuators, a plurality of internal mechanisms, a plurality of ports and a griping area (not shown) that enables holding the control casing and actuating the plurality of actuators with a single hand.

The control casing 300 may comprise at least three ports 301, 302, 303 to couple external elements such as fluid inputting or outputting tubes to the casing. The port 301 may be an oxygen supply port 301, the port 302 may be an aspiration or suction port, and the port 303 be a trigger-transmitting port. The at least three ports may be configured to be selectively opened/closed.

The control casing 300 may also comprise a pair of ports, e.g. concentric ports, for coupling the proximal end portions of the inner guide and outer tube, respectively. In an example, the outer tube may be removably coupled to the control casing.

The control casing 300 may comprise a trigger actuator 310 e.g. a cam, to activate or deactivate the transmission of the trigger. In an example, the pressure exerted may be regulated by rotating the pressing actuator (see the arrows). In an example, the cam may comprise a protrusion which may, as consequence of a rotation, elevate an internal mechanism 343 thereby opening the port 303. The pressing actuator may regulate the transmission of the trigger. The trigger actuator 310 may control the transmission of the trigger through the inner guide to the outer tube. In some examples, the trigger actuator 310 may operate a trigger generator. Examples of trigger generators may be a heater, a pressure generator and/or electrical source.

The control casing 300 may also comprise a fluid flow actuator 320, e.g. sliding actuator, for selectively inputting/outputting fluids through the inner guide. The fluid flow actuator may comprise a protrusion which may elevate, upon movement, an internal mechanism 341, 342 connecting the protrusion of the fluid flow actuator with a port thereby enabling opening the port. In an example, the fluid flow actuator may comprise three positions: a supply position, a suction position and a neutral position.

In FIG. 11 the fluid flow actuator is shown in a neutral position in which there may not be any fluid flow, i.e. there may be no fluid suction nor fluid supply, as the protrusion may not elevate any internal mechanism. In an example, to set the fluid flow actuator in the supply position the actuator may be moved towards the internal mechanism 341, e.g. to the left, thereby opening the port and permitting the fluid supply. Besides, to set the fluid flow actuator in the suction position, the actuator may be moved towards the internal mechanism 342, e.g. to the right, thereby opening the port and enabling the fluid suction.

In some examples (not shown), the control casing may comprise two ports: a fluid inlet port and a fluid output port. The pressing actuator may, in such cases, be coupled to the inlet port and the fluid output ports and may selectively switch, i.e. open/close the access to each port to e.g. provide oxygen, drugs or to aspirate fluids or take fluid samples.

The control casing 300 may comprise a bending actuator 330 which may regulate the bending angle of the bendable portion of the inner guide. In an example, the bending angle may be a predetermined angle between a range of 60°-180° e.g. 120°. The casing may comprise a bending system e.g. a plurality of cables coupled to the bending actuator, in order to set the bendable portion into the required angle.

The control casing may further comprise a locking element for releasably coupling the outer tube to the control casing. In order to set the medical device in the operating position, the practitioner may actuate a locking actuator (not shown) thereby releasing the outer tube from the control casing and enabling removing the inner guide, thus leaving the outer tube inside the corporal conduit.

In an example, the control casing may further comprise resilient elements 350, e.g. springs, for ensuring the contact of the inter mechanisms with the respective actuators. The number of resilient elements and internal mechanisms may depend, e.g. on the number of actuators.

In some examples, the control casing may comprise a plurality of trigger actuators. For example, the control casing may further comprise additional triggering actuators which may collaborate with the trigger actuator 303 to enable triggering the expansion of the outer tube, e.g. by enabling a heated fluid to flow through a lumen of the inner guide, and then the heat may be transmitted from the inner guide to the outer tube via the pressure-exerting element. In another example, the additional triggering actuator may allow the flow of electric current and/or heated fluid through the inner guide to change the temperature of the outer guide.

Figure 12A:
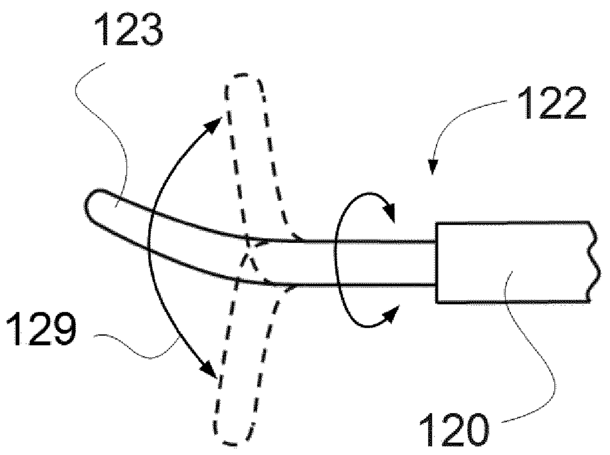
FIG. 12A schematically illustrates a distal end of an inner guide according to an example of the first and/or the second aspect of the present disclosure.
Figure 12B:
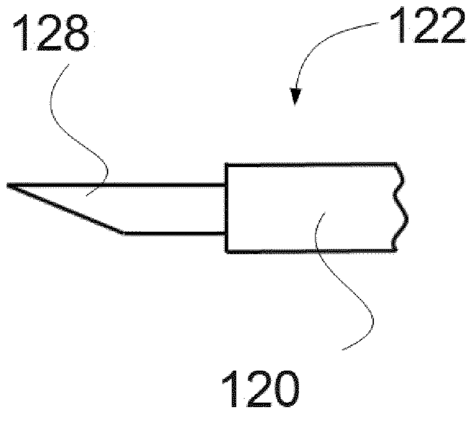
FIG. 12B schematically illustrates a distal end of an inner guide according to an example of the first and/or the second aspect of the present disclosure.

FIGS. 12A and 12B schematically illustrates a distal end of an inner guide according to an example of the first and/or the second aspect of the present disclosure. In these figures, the inner guide 120 comprises a protruding length 122 protruding from the outer tube when the medical device is in the guiding position. For sake of clarity, only the inner guide has been illustrated in these figures.

The protruding length 122 of FIG. 12A comprises a bendable portion 123 and the protruding length 123 of FIG. 12B comprises a cutting element 128. An inner guide with a bendable portion 123 may be used for inserting the inner guide (and the outer tube) through existing corporal conduits. The bendable portion is flexible so as to adapt its shape to the existing corporal conduits. An inner guide with a cutting element 128 may be used for cutting body tissues to create a conduit or passageway between an outside the body and the target zone.

In FIG. 12A, the protruding length 122 comprises a bendable portion 123. The bendable portion of this figure is configured to bend an angle 129. In some examples, the angle 129 may be between 60° and 180°. The bendable portion 123 may be inclined at any position within this angle 129. In the example of this figure the angle 129 substantially correspond to an angle about 180°. In this example, the bendable portion 123 may be maintained substantially aligned to the longitudinal axis of the inner guide or may be bent up to 90° to each side about the longitudinal axis of the inner guide. The bendable portion 123 of this figure may thus adopt any position between 0° and 90° at different sides about the longitudinal axis.

The position of the bendable portion, i.e. the angle of the bendable portion, may be controlled from a control casing according to any of the examples herein disclosed. The control casing may comprise a bendable actuator to control the bending angle of the bendable portion. A cable or a plurality of cables (not shown in this figure) may connect the bendable portion to the bendable actuator. For example, if the cable or the plurality of cables are pulled, the bending angle increases.

In some examples, the bendable portion may extend about 5-10 cm. In some examples, the bendable portion may rotate about the longitudinal axis of the inner guide. This may allow increasing the adaptability to different corporal conduits. Guidance of the outer tube may thus be enhanced.

In FIG. 12B, the inner guide 120 comprises a cutting element 128 arranged at the protruding length 122. This cutting element 128 may be for example a blade or a scalpel. Compared to the bendable portion, the cutting element is rigid and sharpened. The cutting element 128 may be used to cut body tissues for reaching the target zone. The cutting element maybe made e.g. from metal, to facilitate puncturing body tissues.

The inner guide having a cutting element may be used to pass through tissues and to access to a corporal conduct such as a vein. In such examples, the outer tube may be an intravascular line or a catheter. This type of inner guide may also be used for outer tubes that will function as a thoracic catheter and/or in suprapubic urinary drainages.

The medical devices according to any of examples herein disclosed may, in some examples, be used to intubate patients. In such examples, the outer tube may be an endotracheal tube. The inner guide used for intubating patients may comprise a bendable portion according to any of the examples herein disclosed.

In any case, the medical devices according to any of examples herein disclosed may enable translumilarly accessing a corporal conduit.

For reasons of completeness, various aspects of the invention are set out in the following numbered clauses:

Clause 1. A medical device for enabling transluminal access to a corporal conduit, the device comprising: an inner guide comprising a distal end portion; an outer tube configured to receive the distal end portion of inner guide therein, wherein the outer tube comprises a distal end portion; and a pressure-exerting element arranged at the distal end portion of the inner guide, the pressure-exerting element configured to exert a pressure to the distal end portion of the outer tube for releasably coupling the inner guide with the outer tube.

Clause 2. The medical device according to clause 1, wherein the pressure-exerting element is configured to deform between a deployed state for coupling the inner guide with the outer tube and a deployed state for decoupling the inner guide from the outer tube.

Clause 3. The medical device according to clause 1 or 2, wherein the inner guide is removable from the outer tube when the pressure-exerting element is in the undeployed state.

Clause 4. The medical device according to any of clauses 1-3, wherein the inner guide is a tube comprising an internal passageway for inputting and outputting fluids from the corporal conduit.

Clause 5. The medical device according to any of clauses 1-4, wherein the pressure-exerting element is arranged at the outer side of the inner guide.

Clause 6. The medical device according to any of clauses 1-5, wherein the pressure-exerting element comprises a length extending longitudinally along a portion of the distal end portion of the inner guide.

Clause 7. The medical device according to any of clauses 1-6, wherein the inner guide protrudes a protruding length from the outer tube.

Clause 8. The medical device according to any of clauses 1-7, wherein a portion of the distal end portion of the inner guide protrudes a length from the distal end portion of the outer tube.

Clause 9. The medical device according to any of clauses 1-8, wherein the distal end portion of the inner guide comprises a bendable portion, optionally the distal tip may be rigid.

Clause 10. The medical device according to any of clauses 1-9, further comprising a control casing having a plurality of actuators and a gripping area for being held with a single hand thereby enabling holding the casing and actuating the plurality of actuators with a single hand, optionally one of the plurality of actuators being a triggering actuator.

Clause 11. The medical device according to clause 10, wherein one of the plurality of actuators is a pressure actuator for controlling the pressure of the pressure-exerting element.

Clause 12. The medical device according to clause 10 or 11, wherein one of the plurality of actuators is a fluid flow actuator for inputting and outputting fluids.

Clause 13. The medical device according to any of clauses 10-12, wherein one of the plurality of actuators is a bending actuator for bending the distal end portion of the inner guide at a predetermined angle.

Clause 14. The medical device according to any of clauses 1-13, wherein the pressure-exerting element is an inflatable cuff.

Clause 15. The medical device according to any of clauses 1-14, wherein the pressure-exerting element extends longitudinally along the inner guide thereby substantially corresponding to the distal end portion of the outer tube.

Clause 16. The medical device according to any of clauses 8-15, wherein the outer tube is removably attached to the control casing.

Clause 17. The medical device according to any of clauses 1-16, wherein, at operating position, the distal end portion of the outer tube is fixedly secured within the corporal conduit, optionally via an inflatable cuff.

Clause 18. The medical device according to any of clauses 1-17, wherein the distal end portion of the outer tube is configured to be expanded by the pressure exerted by the pressure-exerting element for shifting the medical device from the guiding position to the operating position.

Clause 19. The medical device according to clause 18, wherein the pressure exerted by the pressure-exerting element for setting the medical into the operating position is greater than the elastic limit of the distal end portion of the outer tube.

Clause 20. The medical device according to any of clauses 1-17, wherein the pressure-exerting element is in a deployed state for coupling the inner guide with the outer tube when the medical device is in the guiding position; and wherein the pressure-exerting element in the deployed state comprises a projecting portion projecting from the distal end portion of the outer tube towards the distal end portion of the inner tube, thereby forming a gradually increasing diameter gradient.

Clause 21. The medical device according to any of clauses 1-20, wherein the outer tube is an endotracheal tube.

Clause 22. A medical device for enabling a communication between a target zone within a body and an outside of the body, the device comprising: an inner guide; an outer tube extending from a rear end to a distal end and having an internal cavity, wherein the internal cavity is configured to receive the inner guide therein; wherein the medical device is configured to shift from a guiding position for accessing from an outside of the body to the target zone to an operating position for enabling the communication between the outside of the body and the target zone; wherein when the medical device is in the guiding position, the internal cavity of the outer tube substantially fits the inner guide for traveling together towards the target zone; and wherein when the medical device is in the operating position, the distal end of the outer tube is at the target zone and the rear end of the outer tube is outside the body; and wherein the internal cavity of the outer tube is configured to change in shape in response to a trigger to release the inner guide from the outer tube, thereby shifting the medical device from the guiding position to the operating position.

Clause 23. The medical device according to clause 22, wherein the outer guide comprises a shape memory material.

Clause 24. The medical device according to any of clauses 22-23, wherein the inner guide is removable from the outer tube when the shape of the internal cavity of the outer tube changes in response to the trigger.

Clause 25. The medical device according to any of clauses 22-24, wherein the change in shape of the internal cavity of the outer tube comprises increasing an inner diameter of the internal cavity.

Clause 26. The medical device according to any of clauses 22-25, wherein the change in shape of the internal cavity of the outer tube comprises changing the shape of an outer surface of the outer tube.

Clause 27. The medical device according to any of clauses 22-26, wherein the trigger to cause a change of the shape of the internal cavity of the outer guide comprises at least one of: a temperature variation, a voltage variation, a pH variation and a pressure variation.

Clause 28. The medical device according to any of clauses 22-27, wherein the inner guide is configured to transmit the trigger.

Clause 29. The medical device according to clause 28, wherein the inner guide comprises a pair of electrically conductive elements in contact with an internal surface defining the internal cavity of the outer tube when the medical device is in the guiding position to generate a voltage variation through the outer guide.

Clause 30. The medical device according to any of clauses 28-29, wherein the inner guide comprises a heater to generate a temperature variation on the outer guide when the medical device is in the guiding position.

Clause 31. The medical device according to clause 30, wherein heater comprises an electrical resistance and/or a thermal fluid path for flowing a fluid flow at a predetermined temperature therethrough.

Clause 32. The medical device according to any of clauses 22-31, wherein the inner guide comprises a pressure exerting element to exert a pressure on the outer guide.

Clause 33. The medical device according to any of clauses 22-32, wherein the inner guide is a tube comprising an internal passageway for inputting and outputting fluids from the corporal conduit.

Clause 34. The medical device according to any of clauses 22-33, wherein the inner guide protrudes a protruding length from the outer tube.

Clause 35. The medical device according to clause 34, wherein the inner guide comprises a bendable portion arranged at the protruding length.

Clause 36. The medical device according to clause 35, wherein the bendable portion is configured to bend an angle between 60°-180°.

Clause 37. The medical device according to clause 34, wherein the inner guide comprises a cutting element arranged at the protruding length.

Clause 38. The medical device according to any of clauses 22-37, further comprising a control casing having a plurality of actuators and a gripping area for being held with a single hand thereby enabling holding the casing and actuating the plurality of actuators with a single hand.

Clause 39. The medical device according to clause 38, wherein one of plurality of actuators is a trigger actuator for activating the transmission of the trigger by the inner guide.

Clause 40. The medical device according to any of clauses 37-39, wherein one of the plurality of actuators is a fluid flow actuator for inputting and outputting fluids.

Clause 41. The medical device according to any of clauses 37-40, wherein one of the plurality of actuators is a bending actuator for bending a bendable portion of the inner guide at a predetermined angle.

Clause 42. The medical device according to any of clauses 22-41, wherein the outer tube is configured to function as an endotracheal tube, a urinary catheter or a venous catheter when the medical device is in the operation position.

Although only a number of particular embodiments and examples have been disclosed herein, it will be understood by those skilled in the art that other alternative embodiments and/or uses of the disclosed innovation and obvious modifications and equivalents thereof are possible. Furthermore, the present disclosure covers all possible combinations of the particular embodiments described. The scope of the present disclosure should not be limited by particular embodiments, but should be determined only by a fair reading of the claims that follow.

The invention claimed is:

1. A medical device for enabling a fluid communication between a target zone within a body and an outside of the body, wherein the target zone is a corporal conduit or corporal cavity, the device comprising:

an inner guide;

an outer tube extending from a rear end to a distal end and having an internal cavity, wherein the internal cavity is configured to substantially fit and receive the inner guide therein; and wherein the outer tube is an endotracheal tube or a urinary catheter;

wherein the medical device is configured to shift from a guiding position for accessing from an outside of the body to the target zone to an operating position for enabling the communication between the outside of the body and the target zone;

wherein when the medical device is in the guiding position, the internal cavity of the outer tube substantially fits the inner guide for traveling together towards the target zone so that in the guiding position the outer tube and the inner guide travel together from outside of the body towards the target zone;

wherein when the medical device is in the operating position, the distal end of the outer tube is at the target zone and the rear end of the outer tube is outside the body;

wherein the internal cavity of the outer tube is configured to change in shape in response to a trigger to release the inner guide from the outer tube, thereby shifting the medical device from the guiding position to the operating position, wherein when the medical device is at the operating position the change in shape of the outer tube allows the inner guide to be removed from the body;

wherein the inner guide is configured to transmit the trigger to cause a change of the shape of the internal cavity of the outer tube, the trigger comprising at least a temperature variation; and wherein the inner guide is a tube comprising an internal passageway for inputting and outputting fluids from the corporal conduit.

2. The medical device according to claim 1, wherein the outer tube comprises a shape-memory material.

3. The medical device according to claim 1, wherein the inner guide is removable from the outer tube when the shape of the internal cavity of the outer tube changes in response to the trigger.

4. The medical device according to claim 1, wherein the change in shape of the internal cavity of the outer tube comprises increasing an inner diameter of the internal cavity.

5. The medical device according to claim 1, wherein the change in shape of the internal cavity of the outer tube comprises changing the shape of an outer surface of the outer tube.

6. The medical device according to claim 1, wherein the trigger further comprises at least one of: a voltage variation, a pH variation and a pressure variation.

7. The medical device according to claim 1, wherein the inner guide comprises a heater to generate the temperature variation on the outer tube when the medical device is in the guiding position.

8. The medical device according to claim 7, wherein the heater comprises an electrical resistance and/or a thermal fluid path for flowing a fluid flow at a predetermined temperature therethrough.

9. The medical device according to claim 1, wherein the inner guide comprises a pressure exerting element to exert a pressure on the outer tube.

10. The medical device according to claim 1, wherein the inner guide protrudes a protruding length from the outer tube.

11. The medical device according to claim 10, wherein the inner guide comprises a bendable portion arranged at the protruding length.

12. The medical device according to claim 11, wherein the bendable portion is configured to bend at an angle between 60°-180°.

13. The medical device according to claim 1, further comprising a control casing having a plurality of actuators and a gripping area for being held with a single hand thereby enabling holding the casing and actuating the plurality of actuators with the single hand.

14. A method for arranging a transluminal medical device inside a body, the method comprising:

inserting a distal end of an outer tube fitted to an inner guide into a body, wherein the outer tube is an endotracheal tube or a urinary catheter;

guiding the outer tube and the inner guide for traveling together towards a target zone inside the body;

causing a change of the shape of an internal cavity of the outer tube in response to a trigger transmitted by the inner guide, the trigger comprising at least a temperature variation; and removing the inner guide from the tube to enable a communication between the outside of the body and the target zone such that the distal end of the outer tube is at the target zone and a rear end of the outer tube is outside the body.

15. The method according to claim 14, further comprising operating a trigger actuator to transmit the trigger through the inner guide towards the outer tube, wherein the trigger actuator is an actuator of a control casing having a plurality of actuators and a gripping area for being held with a single hand thereby the control casing enabling holding the casing and actuating the plurality of actuators with a single hand.

16. A medical device for enabling a fluid communication between a target zone within a body and an outside of the body, the device comprising:

an inner guide;

an outer tube extending from a rear end to a distal end and having an internal cavity, wherein the outer tube is an endotracheal tube or a urinary catheter, and wherein the internal cavity is configured to receive the inner guide therein;

a control casing having a plurality of actuators and a gripping area for being held with a single hand thereby enabling holding the casing and actuating the plurality of actuators with a single hand;

wherein the medical device is configured to shift from a guiding position for accessing from an outside of the body to the target zone to an operating position for enabling the communication between the outside of the body and the target zone;

wherein when the medical device is in the guiding position, the internal cavity of the outer tube substantially fits the inner guide for traveling together towards the target zone; and wherein when the medical device is in the operating position, the distal end of the outer tube is at the target zone and the rear end of the outer tube is outside the body; and wherein the internal cavity of the outer tube is configured to change in shape in response to a trigger to release the inner guide from the outer tube, thereby shifting the medical device from the guiding position to the operating position;

wherein the inner guide is configured to transmit the trigger to cause a change of the shape of the internal cavity of the outer tube, the trigger comprising at least a temperature variation; and wherein one of the plurality of actuators is a trigger actuator for activating the transmission of the trigger by the inner guide.

17. The medical device according to claim 16, wherein the inner guide is a tube comprises an internal passageway for inputting and outputting fluids to or from inside the body.

* * * * *